US012698253B2

(12) United States Patent
Parvulescu et al.

(10) Patent No.: US 12,698,253 B2
(45) Date of Patent: Aug. 4, 2026

(54) HETEROGENEOUS SYNTHESIS OF METHYLENE DIANILINE

(71) Applicant: BASF SE, Ludwigshafen am Rhein (DE)

(72) Inventors: Andrei-Nicolae Parvulescu, Ludwigshafen am Rhein (DE); Alvaro Gordillo Bolonio, Ludwigshafen am Rhein (DE); Trees Maria De Baerdemaeker, Ludwigshafen am Rhein (DE); Ulrich Mueller, Ludwigshafen am Rhein (DE); Dirk de Vos, Leuven (BE); Ka Yan Cheung, Leuven (BE)

(73) Assignee: BASF SE, Ludwigshafen am Rhein (DE)

( * ) Notice: Subject to any disclaimer, the term of this patent is extended or adjusted under 35 U.S.C. 154(b) by 688 days.

(21) Appl. No.: 17/783,728

(22) PCT Filed: Dec. 11, 2020

(86) PCT No.: PCT/EP2020/085782
§ 371 (c)(1),
(2) Date: Jun. 9, 2022

(87) PCT Pub. No.: WO2021/116419
PCT Pub. Date: Jun. 17, 2021

(65) Prior Publication Data
US 2023/0028994 A1    Jan. 26, 2023

(30) Foreign Application Priority Data
Dec. 13, 2019    (EP) .................................... 19216029

(51) Int. Cl.
*C07C 213/02*        (2006.01)
*B01J 21/06*         (2006.01)
(Continued)

(52) U.S. Cl.
CPC ........... *C07C 213/02* (2013.01); *B01J 21/063* (2013.01); *B01J 21/066* (2013.01); *B01J 21/08* (2013.01);
(Continued)

(58) Field of Classification Search
CPC ..... C07C 213/02; B01J 35/635; B01J 21/063; B01J 21/066; B01J 21/08; B01J 23/06; B01J 23/75; B01J 23/755
See application file for complete search history.

(56) References Cited

U.S. PATENT DOCUMENTS

| | | | | |
|---|---|---|---|---|
| 5,241,119 | A | * | 8/1993 | Clerici et al. ......... C07C 211/49 564/332 |
| 6,410,789 | B1 | * | 6/2002 | Becker et al. ........ C07C 211/00 564/330 |
| 2011/0144368 | A1 | | 6/2011 | Weiner et al. |

FOREIGN PATENT DOCUMENTS

| | | |
|---|---|---|
| EP | 3263547 A1 | 1/2018 |
| JP | 2012131720 A | 7/2012 |

(Continued)

OTHER PUBLICATIONS

Chem. Mater. 2011, 23, 2491-2498 (Masika et al.).*
(Continued)

*Primary Examiner* — Amy C Bonaparte
*Assistant Examiner* — Derek Rhoades
(74) *Attorney, Agent, or Firm* — Lowenstein Sandler LLP

(57) ABSTRACT

The present invention relates to a catalytic material for the preparation of one or more of 4,4'-methylenedianiline, 2,2'-methylenedianiline, 2,4'-methylenedianiline, and oligomers of two or more thereof, the catalytic material comprising an oxidic support, wherein the oxidic support comprises an element $E_{OS1}$ selected from the group consisting of Ti, Zr, Al, Si, and mixtures of two or more thereof, and further comprising a supported material supported on the oxidic (Continued)

support, wherein the supported material comprises an element ESM1 selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb and mixtures of two or more thereof. Further, the present invention relates in particular to a process for the preparation of a catalytic material and to a process for the preparation of one or more of 4,4'-methylenedianiline, 2,2'-methylenedianiline, 2,4'-methylenedianiline and oligomers of two or more thereof.

13 Claims, 2 Drawing Sheets

(51) Int. Cl.
    *B01J 21/08*        (2006.01)
    *B01J 23/06*        (2006.01)
    *B01J 23/75*        (2006.01)
    *B01J 23/755*      (2006.01)
    *B01J 35/63*        (2024.01)

(52) U.S. Cl.
    CPC ............... *B01J 23/06* (2013.01); *B01J 23/75* (2013.01); *B01J 23/755* (2013.01); *B01J 35/635* (2024.01); *B01J 2235/10* (2024.01)

(56) References Cited

FOREIGN PATENT DOCUMENTS

| JP | 2012250971 A | 12/2012 |
| JP | 2013095724 A | 5/2013 |
| KR | 2000-0075625 A | 12/2000 |
| WO | 2010019844 A1 | 2/2010 |
| WO | 2010072504 A1 | 7/2010 |
| WO | 2016005269 A1 | 1/2016 |
| WO | 2018210711 A1 | 11/2018 |

OTHER PUBLICATIONS

Chem. Soc. Rev. 2019, 48, 1095-1149 (Shamzhy et al.).*
Appl. Catal. A Gen. 2006, 307, 128-136 (Perego et al.) (Year: 2006).*
Catal. Today 2015, 259, 19-26 (McCue et al.) (Year: 2015).*
ChemSusChem 2014, 7, 753-764 (Verboekend et al.) (Year: 2014).*
Can. J. Chem. Eng. 2019, 97, 2781-2791 (Bardestani et al.) (Year: 2019).*
C.A. Emeis "Determination of integrated molar extinction coefficients for infrared absorption bands of pyridine adsorbed on solid acid catalysts" in Journal of Catalysis 1993, vol. 141, p. 347-354.
D. Jin et al. disclose in Microporous and Mesoporous Materials 2016, vol. 233, p. 109-116.
M. Haus et al. disclose in Chemical Engineering Science 2017, vol. 167, p. 317.
M. Velthoen et al. "Probing acid sites in solid catalysts with pyridine UV-Vis spectroscopy" in Physical Chemistry Chemical Physics 2018, vol. 20, p. 21647-21659.
De Baerdemaeker Trees et al: Bimetallic Zn and Hf on Silica Catalysts for the Conversion of Ethanol to 1,3-Butadiene1, ACS Catalysis, vol. 5, No. 6, Jun. 5, 2015 (Jun. 5, 2015), pp. 3393-3397.
International Search Report for PCT/EP2020/085782 mailed Feb. 2, 2021, 3 pages.
Cheung et al., "Lewis acid solid catalysts for the synthesis of methylenedianiline from aniline and formaldehyde," Journal of Catalysis, 400 (2021), pp. 114-123.

* cited by examiner

HETEROGENEOUS SYNTHESIS OF METHYLENE DIANILINE

CROSS REFERENCE TO RELATED APPLICATION(S)

The present application is a national stage entry under 35 U.S.C. § 371 of International Application No. PCT/EP2020/085782, filed on Dec. 11, 2020, which claims priority to European Patent Application No. 19216029.9, filed on Dec. 13, 2019, the entirety of which are incorporated herein by reference in their entirety.

FIELD OF THE INVENTION

The present invention relates to a catalyst for producing in particular 4,4'-methylenedianiline (also abbreviated herein as MDA; IUPAC: Bis(4-aminophenyl)methane), a process for the preparation of the catalyst, its use and a process for producing in particular 4,4'-methylenedianiline using said catalyst.

BACKGROUND OF THE INVENTION 4,4'-methylenedianiline (MDA) is an important precursor for polyurethanes, in particular for the production of 4,4'-methylene diphenyl diisocyanate (MDI). On an industrial scale, 4,4'-methylenedianiline is prepared by the condensation reaction of aniline and formaldehyde to N,N'-diphenyl-methylenediamine (further referred to as "aminal") and subsequent rearrangement reactions in the presence of hydrochloric acid as catalyst. In addition to N,N'-diphenyl-methylenediamine, further intermediate benzylaniline species may form such as aminobenzylaniline intermediates where one of the two internal methylation reactions has already taken place. Thus, it is also referred to said intermediates as "ABA", "para-ABA", or "ortho-ABA". Such intermediates can also convert in the subsequent rearrangement reactions. Usually, MDA is yielded as the major component of a technical mixture with a varying content of tri- and polymers with varying substitution patterns (ortho and para), which may then be processed to polyurethane.

The conventional homogeneous preparation of MDA catalyzed by hydrochloric acid has several drawbacks, e.g. in terms of process handling. In particular, use of hydrochloric acid as catalyst in the preparation causes several problems, including the handling of hydrochloric acid, which may corrode storage and disposal containers. Further, environmental problems are caused by the necessity of neutralizing the hydrochlorides, in particular of the desired MDA, prior to further conversion reactions. Due to said major drawbacks, which are aligned to the use of hydrochloric acid as catalyst, it is of considerable commercial interest to substitute the mineral acid by a solid acid catalyst. Moreover, a solid catalyst could be regenerated, thus, lowering the total costs of raw materials. In this regard, zeolites have been tested earlier since they have Brønstedt acidity, high thermal and mechanical stability.

WO 2016/005269 A1 relates to a process for the preparation of di- and polyamines of the diphenylmethane series by the rearrangement of a condensation product of aniline and a methylene group-supplying agent wherein said condensation product is reacted in the presence of at least one solid zeolite catalyst partially or fully ion-exchanged to the protonic form. In this connection, zeolites of the framework structure type FAU, MFI, MOR, HEU, and BEA are disclosed.

M. Haus et al. disclose in Chemical Engineering Science 2017, vol. 167, p. 317 a study on Advanced kinetic models through mechanistic understanding relative to the population balances for methylenedianiline synthesis. In the experimental section, a commercially available silica-alumina is disclosed as acid catalyst in the experiments for converting an aminal solution.

EP 3 263 547 A1 relates to a production process for di- and polyamines of the diphenylmethane series by the rearrangement of a condensation product of aniline and a methylene group-supplying agent. In this regard, a catalyst was used comprising a specific silica-alumina.

D. Jin et al. disclose in Microporous and Mesoporous Materials 2016, vol. 233, p. 109-116 a study on the change of methylenedianiline activity and selectivity in different pore geometry of zeolites. In particular, the activity and isomers selectivity of the synthesis of methylenedianiline (MDA) from aminal on the various zeolites with different topology structure has been investigated.

JP 2012-131720 A relates to a production method for methylenedianiline derivative(s) (MDA derivative(s)) at high yield and for 4,4'-MDA at high selectivity in the presence of a zeolite catalyst, which may comprise an alkali metal or an alkaline earth metal.

JP 2013-095724 A relates to a production method for an aromatic polyamine at high yield in the presence of a zeolite catalyst, whereby 4,4'-MDA may be obtained at a high selectivity.

JP 2012-250971 A relates to a method for producing an aromatic polyamine in high yield by a reaction in the presence of a specific solid acid catalyst, wherein in particular silica-alumina, silica-titania, silica-zirconia, or a specific zeolite may be used as catalyst. Alternatively, a specific metal oxide may be used as catalyst.

WO 2010/019844 A1 relates to compositions, systems, and methods of forming an amine (e.g., methylenedianiline (MDA)) using an acid catalyst including, for example, a metal oxide-silica catalyst, wherein the metal oxide of a solid acid silica-metal oxide catalyst may comprise alumina. Further, the metal oxide may be selected from the group consisting of $Al_2O_3$, $TiO_2$, $GeO_2$, $SnO_2$, $ZrO_2$, $B_2O_3$, $Nb_2O_5$, $Ta_2O_5$, $V_2O_5$, $MoO_3$, $WO_3$, and combinations thereof. The molar ratio of metal oxide to silica may be in the range of from about 0.01 to about 0.5.

WO 2010/072504 A1 relates to a process for providing methylene-bridged polyphenyl polyamines from aniline and formaldehyde comprising the subsequent steps of a) condensing aniline and formaldehyde, providing a condensate, b) reacting, in a first catalytic reaction step, at a specific temperature said condensate over a solid catalyst being chosen from the group consisting of clays, silicates, silica-aluminas and ion exchange resins, whereby an intermediate mixture is provided, the intermediate mixture comprising amino benzyl amines; c) converting, in a subsequent catalytic reaction step, at a specific temperature said intermediate mixture into methylene-bridged polyphenyl polyamines in the presence of a subsequent solid catalyst being chosen from the group consisting of zeolites, delaminated zeolites and ordered mesoporous materials, thereby providing a methylene-bridged polyphenyl polyamines.

SUMMARY OF THE INVENTION

Therefore, it was an object of the present invention to provide a catalytic material having a high activity and improved lifetime behavior, in particular with regard to the preparation of one or more of 4,4'-methylenedianiline, 2,2'- methylenedianiline, 2,4'-methylenedianiline, and oligomeric compounds thereof. Since 4,4'-methylenedianiline represents the most important product, it is particularly desired to achieve a comparatively high MDA isomer molar ratio expressed as 4,4'-MDA/(2,2'-MDA+2,4'-MDA). Thus, it was a further object of the present invention to provide a catalytic material which can achieve a high MDA isomer molar ratio.

DETAILED DESCRIPTION OF THE INVENTION

Thus, the present invention relates to a novel class of heterogeneous catalysts for the preparation in particular of 4,4'-methylenedianiline based on supported metals on support materials, in particular having a specific Brønsted acidity and a specific Lewis acidity.

Thus, the present invention relates to a catalytic material for the preparation of one or more of 4,4'-methylenedianiline (also designated herein as 4,4'-MDA), 2,2'-methylenedianiline (also designated herein as 2,2'-MDA), 2,4'-methylenedianiline (also designated herein as 2,4'-MDA), and oligomers of two or more thereof, preferably for the preparation of one or more of 4,4'-methylenedianiline, 2,2'-methylenedianiline, and 2,4'-methylenedianiline, more preferably for the preparation of 4,4'-methylenedianiline, the catalytic material comprising an oxidic support, wherein the oxidic support comprises an element $E_{OS1}$ selected from the group consisting of Ti, Zr, Al, Si, and mixtures of two or more thereof, and further comprising a supported material supported on the oxidic support, wherein the supported material comprises an element $E_{SM1}$ selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb, and mixtures of two or more thereof. Thus, the catalytic material comprises an oxidic support and a supported material wherein the supported material is supported on the oxidic support.

Further, the present invention relates to a process for the preparation of a catalytic material, preferably for the preparation of a catalytic material according to any one of the embodiments disclosed herein, the process comprising (i) preparing a mixture comprising a liquid solvent system, a source of an oxidic support comprising an element $E_{OS1}$ selected from the group consisting of Ti, Zr, Al, Si, and mixtures of two or more thereof, a source of an element $E_{SM1}$ selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb and mixtures of two or more thereof, and optionally a source of an element $E_{SM2}$ selected from groups 3-14 of the periodic system of elements, rare earth metals, and mixtures of two or more thereof, wherein the optional $E_{SM2}$ is different to $E_{SM1}$, obtaining a precursor of the catalytic material;

(ii) calcining the precursor of the catalytic material in a gas atmosphere, obtaining the catalytic material.

Yet further, the present invention relates to a catalytic material obtainable and/or obtained by the process of any one of the embodiments disclosed herein.

Yet further, the present invention relates to a process for the preparation of one or more of 4,4'-methylenedianiline, 2,2'-methylenedianiline, 2,4'-methylenedianiline, and oligomers of two or more thereof, preferably for the preparation of one or more of 4,4'-methylenedianiline, 2,2'-methylenedianiline, and 2,4'-methylenedianiline, more preferably for the preparation of 4,4'-methylenedianiline, the process comprising (1) providing a reactor comprising a reaction zone, wherein the reaction zone comprises a catalytic material according to any one of the embodiments disclosed herein;

(2) providing a feed into the reaction zone according to (1), wherein the feed comprises one or more of aniline, formaldehyde, and N,N'-diphenylmethylenediamine;

(3) converting the feed under reaction conditions in the reaction zone; obtaining a product mixture comprising one or more of 4,4'-methylenedianiline, 2,2'-methylenedianiline, 2,4'-methylenedianiline, and oligomers of two or more thereof;

(4) separating the product mixture from the reaction zone.

Yet further, the present invention relates to a catalytic material according to any one of the embodiments disclosed herein in a process for the preparation of one or more of 4,4'-methylenedianiline, 2,2'-methylenedianiline, 2,4'-methylenedianiline, and oligomers of two or more thereof, preferably for the preparation of one or more of 4,4'-methylenedianiline, 2,2'-methylenedianiline, and 2,4'-methylenedianiline, more preferably for the preparation of 4,4'-methylenedianiline. With respect to the catalytic material, it is preferred that $E_{OS1}$ is Al and/or Si. It is particularly preferred that $E_{OS1}$ is Si.

It is preferred that the oxidic support comprises titania, zirconia, alumina, or silica. It is preferred that the oxidic support consists of titania, zirconia, alumina, or silica.

It is preferred that from 95 to 100 weight-% of the oxidic support consists of $E_{OS1}$, O, and H, more preferably from 97 to 100 weight-%, more preferably from 98 to 100 weight-%, more preferably from 99 to 100 weight-%, based on the total weight of the oxidic support.

It is preferred as an alternative that the oxidic support comprises, preferably consists of, a zeolitic material. In this regard, it is preferred that the zeolitic material comprises $E_{OS1}$ and optionally $E_{OS2}$ in its framework structure, wherein $E_{OS1}$ more preferably is Si, and wherein $E_{OS2}$ more preferably is Al, wherein the zeolitic material more preferably comprises, preferably consists of, a 10-membered ring pore zeolitic material and/or a 12-membered ring pore zeolitic material. Further, it is preferred that the zeolitic material comprises $E_{OS1}$ and $E_{OS2}$ in its framework structure, wherein $E_{OS1}$ more preferably is Si, and wherein $E_{OS2}$ more preferably is Al, wherein the zeolitic material exhibits a molar ratio of $E_{OS1}$ to $E_{OS2}$ in the range of from 5 to 50, preferably in the range of from 10 to 20, more preferably in the range of from 13 to 16. Further, it is preferred that the 10-membered ring pore zeolitic material has a framework structure type selected from the group consisting of FER, TON, MTT, SZR, MFI, MWW, AEL, HEU, AFO, a mixture of two or more thereof and a mixed type of two or more thereof, preferably selected from the group consisting of FER, TON, MFI, MWW, AEL, HEU, AFO, a mixture of two or more thereof and a mixed type of two or more thereof, more preferably selected from the group consisting of MFI and MWW, wherein more preferably the 10-membered ring pore zeolitic material has a framework type MWW. Further, it is preferred that the 10-membered ring pore zeolitic material having a framework structure type MWW is selected from the group consisting of MCM-22, ERB-1, ITQ-1, PSH-3, and SSZ-25 and MCM-22, including mixtures of two or more thereof, wherein more preferably the 10-membered ring pore zeolitic material having a framework structure type MWW comprises MCM-22, wherein more preferably the 10-membered ring pore zeolitic material having a framework structure type MWW is MCM-22. Further, it is preferred that the 12-membered ring pore zeolitic material has a framework structure type selected from the group consisting of BEA, FAU, USY, GME, MOR, OFF, a mixture of two or more thereof and a mixed type of two or more thereof, preferably selected from the group consisting of BEA, USY, FAU, a mixture of two or more thereof and a mixed type of two or more thereof, wherein more preferably the 12-membered ring pore zeolitic material has a framework type FAU. Further, it is preferred that the zeolitic material having a framework structure type FAU is selected from the group consisting of ZSM-3, Faujasite, [Al—Ge—O]-FAU, CSZ-1, ECR-30, Zeolite X, Zeolite Y, LZ-210, SAPO-37, ZSM-20, Na-X, US-Y, Na-Y, [Ga—Ge—O]-FAU, Li-LSX, [Ga—Al—Si—O]-FAU, and [Ga—Si—O]-FAU, including mixtures of two or more thereof, preferably from the group consisting of ZSM-3, Faujasite, CSZ-1, ECR-30, Zeolite X, Zeolite Y, LZ-210, ZSM-20, Na-X, US-Y, Na-Y, and Li-LSX, including mixtures of two or more thereof, more preferably from the group consisting of Faujasite, Zeolite X, Zeolite Y, Na-X, US-Y, and Na-Y, including mixtures of two or more thereof, more preferably from the group consisting of Faujasite, Zeolite X, and Zeolite Y, including mixtures of two or more thereof, wherein more preferably the zeolitic material having a framework structure type FAU comprises, more preferably consists of, zeolite X and/or zeolite Y, preferably zeolite Y.

It is preferred that the oxidic support further comprises an element $E_{OS2}$ selected from group 4, 13 and 14 elements of the periodic system of elements, including mixtures of two or more thereof, wherein $E_{OS2}$ is different to $E_{OS1}$.

In the case where the oxidic support further comprises an element $E_{OS2}$, it is preferred that $E_{OS2}$ is selected from the group consisting of Ti, Zr, Al, Si, Sn, and mixtures of two or more thereof, wherein $E_{OS2}$ preferably comprises Al and/or Si, wherein more preferably $E_{OS2}$ comprises Al. It is particularly preferred that $E_{OS2}$ consists of Al.

Further in the case where the oxidic support further comprises an element $E_{OS2}$, it is preferred that the oxidic support comprises silica-alumina, titania-silica, titania-alumina, zirconia-silica, zirconia-alumina, or titania-zirconia, wherein more preferably the oxidic support comprises silica-alumina. It is particularly preferred that the oxidic support consists of silica-alumina, titania-silica, titania-alumina, zirconia-silica, zirconia-alumina, or titania-zirconia, wherein more preferably the oxidic support consists of silica-alumina.

It is preferred that from 95 to 100 weight-% of the oxidic support consists of $E_{OS1}$, $E_{OS2}$, O, and H, more preferably from 97 to 100 weight-%, more preferably from 98 to 100 weight-%, more preferably from 99 to 100 weight-%, based on the total weight of the oxidic support.

It is preferred that $E_{SM1}$ is selected from the group consisting of Sc, Y, La, Ce, Nd, Pr, Hf, Cr, Fe, Co, Ni, Cu, Zn, Pb, Zr, and mixtures of two or more thereof, more preferably from the group consisting of Sc, La, Ce, Hf, Cr, Fe, Ni, Cu, Zn, Zr, and mixtures of two or more thereof, more preferably from the group consisting of Sc, La, Ce, Hf, Fe, Zn, Zr, and mixtures of two or more thereof, more preferably from the group consisting of Sc, Hf, Fe, Zn, Zr, and mixtures of two or more thereof, and mixtures of two or more thereof, wherein more preferably $E_{SM1}$ is Hf and/or Fe, wherein more preferably $E_{SM1}$ is Hf.

It is preferred that the catalytic material comprises $E_{SM1}$, calculated as element, in an amount in the range of from 0.1 to 10 weight-%, more preferably in the range of from 1 to 5 weight-%, more preferably in the range of from 1.1 to 4.9 weight-%, more preferably in the range of from 1.2 to 4.5 weight-%, more preferably in the range of from 2.0 to 4.0 weight-%, more preferably in the range of from 2.5 to 3.5 weight-%, based on the total weight of the oxidic support.

It is preferred that from 95 to 100 weight-% of the supported material consists of $E_{SM1}$, O and H, more preferably from 97 to 100 weight-%, more preferably from 98 to 100 weight-%, more preferably from 99 to 100 weight-%, based on the total weight of the supported material.

It is preferred that the supported material further comprises an element $E_{SM2}$ selected from groups 3-14 of the periodic system of elements, rare earth metals, and mixtures of two or more thereof, wherein $E_{SM2}$ is different to $E_{SM1}$.

In the case where the supported material further comprises an element $E_{SM2}$, it is preferred that $E_{SM2}$ is selected from groups 3, 4, 5, 6, 8, 10, 11, 12, 14, rare earth metals, and mixtures of two or more thereof, more preferably from the group consisting of Sc, Y, La, Ce, Nd, Pr, Ti, Zr, Hf, V, Nb, Ta, Cr, Mo, W, Fe, Co, Ni, Cu, Zn, Ge, Sn, Pb, and mixtures of two or more thereof, more preferably from the group consisting of Sc, La, Ce, Zr, Hf, Nb, Ta, Cr, Fe, Ni, Cu, Zn, Sn, and mixtures of two or more thereof, more preferably from the group consisting of Sc, La, Ce, Zr, Hf, Nb, Ta, Fe, Zn, Sn, and mixtures of two or more thereof, more preferably from the group consisting of Sc, Zr, Hf, Nb, Fe, Zn, Sn, and mixtures of two or more thereof, more preferably from the group consisting of Sc, Zr, Hf, Nb, Fe, Zn, and mixtures of two or more thereof, wherein more preferably $E_{SM2}$ is Zn.

Further in the case where the supported material further comprises an element $E_{SM2}$, it is preferred that the catalytic material comprises $E_{SM2}$, calculated as element, in an amount in the range of from 0.1 to 3 weight-%, more preferably in the range of from 0.2 to 1.0 weight-%, more preferably in the range of from 0.3 to 0.8 weight-%, more preferably in the range of from 0.4 to 0.6 weight-%, based on the total weight of the oxidic support.

Further in the case where the supported material further comprises an element $E_{SM2}$, it is preferred that from 95 to 100 weight-% of the supported material consists of $E_{SM1}$, $E_{SM2}$, O, and H, more preferably from 97 to 100 weight-%, more preferably from 98 to 100 weight-%, more preferably from 99 to 100 weight-%, based on the total weight of the supported material.

It is preferred that from 95 to 100 weight-% of the catalytic material consists of the oxidic support and the supported material, more preferably from 97 to 100 weight-%, more preferably from 98 to 100 weight-%, more preferably from 99 to 100 weight-%, based on the total weight of the catalytic material.

It is preferred that the catalytic material exhibits a type IV nitrogen adsorption/desorption isotherm, wherein the nitrogen adsorption/desorption isotherm is preferably determined according to Reference Example 3 disclosed herein.

It is preferred that the catalytic material has a total pore volume in the range of from 0.5 to 1.0 cm$^3$/g, more preferably in the range of from 0.65 to 0.80 cm$^3$/g, more preferably in the range of from 0.70 to 0.76 cm$^3$/g, more preferably in the range of from 0.72 to 0.74 cm$^3$/g, wherein the total pore volume is preferably determined according to Reference Example 4 disclosed herein.

It is preferred that the catalytic material has a BET specific surface area in the range of from 100 to 250 m$^2$/g, more preferably in the range of from 150 to 200 m$^2$/g, more preferably in the range of from 160 to 190 m$^2$/g, more preferably in the range of from 170 to 180 m$^2$/g, wherein the BET specific surface area is preferably determined according to Reference Example 6 disclosed herein.

It is preferred that the catalytic material shows in the temperature programmed desorption of ammonia ($NH_3$-TPD) a desorption peak having a maximum in the range of from 200 to 250° C., more preferably in the range of from 210 to 240° C., more preferably in the range of from 220 to 230° C., wherein the temperature programmed desorption of ammonia ($NH_3$-TPD) preferably shows only one maximum, wherein the temperature programmed desorption of ammonia ($NH_3$-TPD) is preferably determined according to Reference Example 7 disclosed herein.

It is preferred that the catalytic material shows no Brønstedt acidity in the temperature programmed desorption of ammonia ($NH_3$-TPD), wherein the temperature programmed desorption of ammonia ($NH_3$-TPD) is preferably determined according to Reference Example 7 disclosed herein.

It is preferred that the catalytic material exhibits a Lewis acid site density in the range of from 25 to 100 µmol/g, preferably in the range of from 50 to 75 µmol/g, more preferably in the range of from 60 to 65 µmol/g, at a temperature of 150° C., preferably determined as described in Reference Example 1.

It is preferred that the catalytic material exhibits a Brønsted acid site density of at most 5 µmol/g, more preferably of at most 2 µmol/g, more preferably of at most 1 µmol/g, determined as described in Reference Example 1.

It is preferred that the catalytic material exhibits a selectivity towards one or more of 4,4'-methylenedianiline, 2,2'-methylenedianiline, 2,4'-methylenedianiline, and oligomers of two or more thereof, preferably towards one or more of 4,4'-methylenedianiline, 2,2'-methylenedianiline, and 2,4'-methylenedianiline, in the range of from 4 to 100%, more preferably in the range of from 30 to 90%, more preferably in the range of from 45 to 75%, preferably determined as described in Example 4.

It is preferred that the catalytic material exhibits a molar isomer ratio of 4,4'-methylenedianiline to 2,2'-methylenedianiline and 2,4'-methylenedianiline in the range of from 0.1 to 20, preferably in the range of from 0.5 to 15, more preferably in the range of from 1 to 10, more preferably in the range of from 2.0 to 5.0, more preferably in the range of from 3.5 to 4.5, preferably determined as described in Example 4.

Further, the present invention relates to a process for the preparation of a catalytic material, preferably for the preparation of a catalytic material according to any one of the embodiments disclosed herein, the process comprising (i) preparing a mixture comprising a liquid solvent system, a source of an oxidic support comprising an element $E_{OS1}$ selected from the group consisting of Ti, Zr, Al, Si, and mixtures of two or more thereof, a source of an element $E_{SM1}$ selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb and mixtures of two or more thereof, and optionally a source of an element $E_{SM2}$ selected from groups 3-14 of the periodic system of elements, rare earth metals, and mixtures of two or more thereof, wherein the optional $E_{SM2}$ is different to $E_{SM1}$, obtaining a precursor of the catalytic material;

(ii) calcining the precursor of the catalytic material in a gas atmosphere, obtaining the catalytic material.

It is preferred that preparing a mixture in (i) is carried out at a temperature in the range of from 10 to 35° C., more preferably in the range of from 15 to 30° C., more preferably in the range of from 20 to 25° C.

It is preferred that the liquid solvent system comprises one or more of water, deionized water, ultrapure water, methanol, ethanol, isopropanol, tetrahydrofuran, and acetic acid. It is particularly preferred that the liquid solvent system comprises ultrapure water.

It is preferred that $E_{OS1}$ comprises Al and/or Si, more preferably comprises Si. It is particularly preferred that $E_{OS1}$ consists of Si.

It is preferred that the source of an oxidic support further comprises an element $E_{OS2}$ selected from group 4, 13 and 14 elements of the periodic system of elements, including mixtures of two or more thereof, wherein $E_{OS2}$ is different to $E_{OS1}$.

In the case where the source of an oxidic support further comprises an element $E_{OS2}$, it is preferred that $E_{OS2}$ is selected from the group consisting of Ti, Zr, Al, Si, Sn, and mixtures of two or more thereof, wherein $E_{OS2}$ more preferably comprises Al and/or Si, wherein more preferably $E_{OS2}$ comprises Al. It is particularly preferred that $E_{OS2}$ consists of Al.

It is preferred that the source of an oxidic support comprises one or more of silica, alumina, titanic, zirconia, silica-alumina, titania-silica, titania-alumina, zirconia-silica, zirconia-alumina, titanic-zirconia, more preferably one or more of silica, alumina, silica-alumina, wherein more preferably the source of an oxidic support comprises silica-alumina.

It is preferred as an alternative that the source of an oxidic support comprises, preferably consists of, a zeolitic material. In this regard, it is preferred that the zeolitic material comprises $E_{OS1}$ and optionally $E_{OS2}$ in its framework structure, wherein $E_{OS1}$ more preferably is Si, and wherein $E_{OS2}$ more preferably is Al, wherein the zeolitic material more preferably comprises, preferably consists of, a 10-membered ring pore zeolitic material and/or a 12-membered ring pore zeolitic material. Further, it is preferred that the zeolitic material comprises $E_{OS1}$ and $E_{OS2}$ in its framework structure, wherein $E_{OS1}$ more preferably is Si, and wherein $E_{OS2}$ more preferably is Al, wherein the zeolitic material exhibits a molar ratio of $E_{OS1}$ to $E_{OS2}$ in the range of from 5 to 50, preferably in the range of from 10 to 20, more preferably in the range of from 13 to 16. Further, it is preferred that the 10-membered ring pore zeolitic material has a framework structure type selected from the group consisting of FER, TON, MTT, SZR, MFI, MWW, AEL, HEU, AFO, a mixture of two or more thereof and a mixed type of two or more thereof, preferably selected from the group consisting of FER, TON, MFI, MWW, AEL, HEU, AFO, a mixture of two or more thereof and a mixed type of two or more thereof, more preferably selected from the group consisting of MFI and MWW, wherein more preferably the 10-membered ring pore zeolitic material has a framework type MWW. Further, it is preferred that the 10-membered ring pore zeolitic material having a framework structure type MWW is selected from the group consisting of MCM-22, ERB-1, ITQ-1, PSH-3, and SSZ-25 and MCM-22, including mixtures of two or more thereof, wherein more preferably the 10-membered ring pore zeolitic material having a framework structure type MWW comprises MCM-22, wherein more preferably the 10-membered ring pore zeolitic material having a framework structure type MWW is MCM-22. Further, it is preferred that the 12-membered ring pore zeolitic material has a framework structure type selected from the group consisting of BEA, FAU, USY, GME, MOR, OFF, a mixture of two or more thereof and a mixed type of two or more thereof, preferably selected from the group consisting of BEA, USY, FAU, a mixture of two or more thereof and a mixed type of two or more thereof, wherein more preferably the 12-membered ring pore zeolitic material has a framework type FAU. Further, it is preferred that the zeolitic material having a framework structure type FAU is selected from the group consisting of ZSM-3, Faujasite, [Al—Ge—O]-FAU, CSZ-1, ECR-30, Zeolite X, Zeolite Y, LZ-210, SAPO-37, ZSM-20, Na-X, US-Y, Na-Y, [Ga—Ge—O]-FAU, Li-LSX, [Ga—Al—Si—O]-FAU, and [Ga—Si—O]-FAU, including mixtures of two or more thereof, preferably from the group consisting of ZSM-3, Faujasite, CSZ-1, ECR-30, Zeolite X, Zeolite Y, LZ-210, ZSM-20, Na-X, US-Y, Na-Y, and Li-LSX, including mixtures of two or more thereof, more preferably from the group consisting of Faujasite, Zeolite X, Zeolite Y, Na-X, US-Y, and Na-Y, including mixtures of two or more thereof, more preferably from the group consisting of Faujasite, Zeolite X, and Zeolite Y, including mixtures of two or more thereof, wherein more preferably the zeolitic material having a framework structure type FAU comprises, more preferably consists of, zeolite X and/or zeolite Y, preferably zeolite Y.

It is preferred that the source of the element $E_{SM1}$ is a salt, wherein the salt preferably comprises one or more of a halide, a nitrate, an acetate, a sulfate, a phosphate, and a carbonate, more preferably one or more of a fluoride, a chloride, a bromide, and an iodide, more preferably the source of the element $E_{SM1}$ comprises a chloride. It is particularly preferred that the source of the element $E_{SM1}$ consists of a chloride.

It is preferred that $E_{SM1}$ is selected from the group consisting of Sc, Y, La, Ce, Nd, Pr, Hf, Cr, Fe, Co, Ni, Cu, Zn, Pb, Zr, and mixtures of two or more thereof, more preferably from the group consisting of Sc, La, Ce, Hf, Cr, Fe, Ni, Cu, Zn, Zr, and mixtures of two or more thereof, more preferably from the group consisting of Sc, La, Ce, Hf, Fe, Zn, Zr, and mixtures of two or more thereof, more preferably from the group consisting of Sc, Hf, Fe, Zn, Zr, and mixtures of two or more thereof. It is particularly preferred that $E_{SM1}$ is Hf and/or Fe, more preferably Hf.

It is preferred that the mixture prepared in (i) comprises the source of an element $E_{SM2}$, wherein $E_{SM2}$ is different to $E_{SM1}$.

In the case where the mixture prepared in (i) comprises the source of an element $E_{SM2}$, wherein $E_{SM2}$ is different to $E_{SM1}$, it is preferred that $E_{SM2}$ is selected from groups 3, 4, 5, 6, 8, 10, 11, 12, 14, and rare earth metals, and mixtures of two or more thereof, more preferably from the group consisting of Sc, Y, La, Ce, Nd, Pr, Ti, Zr, Hf, V, Nb, Ta, Cr, Mo, W, Fe, Co, Ni, Cu, Zn, Ge, Sn, Pb, and mixtures of two or more thereof, more preferably from the group consisting of Sc, La, Ce, Zr, Hf, Nb, Ta, Cr, Fe, Ni, Cu, Zn, Sn, and mixtures of two or more thereof, more preferably from the group consisting of Sc, La, Ce, Zr, Hf, Nb, Ta, Fe, Zn, Sn, and mixtures of two or more thereof, more preferably from the group consisting of Sc, Zr, Hf, Nb, Fe, Zn, Sn, and mixtures of two or more thereof, more preferably from the group consisting of Sc, Zr, Hf, Nb, Fe, Zn, and mixtures of two or more thereof. It is particularly preferred that $E_{SM2}$ is Zn.

It is preferred that in the mixture prepared in (i) the weight ratio of the source of an element $E_{SM1}$, calculated as element, to the source of an oxidic support, calculated as the oxide or mixed oxide of the element $E_{OS1}$ and the optional element $E_{OS2}$, is in the range of from 0.1 to 10 weight-%, more preferably in the range of from 1 to 5 weight-%, more preferably in the range of from 1.1 to 4.9 weight-%, more preferably in the range of from 1.2 to 4.5 weight-%, more preferably in the range of from 2.0 to 4.0 weight-%, more preferably in the range of from 2.5 to 3.5 weight-%.

It is preferred that in the mixture prepared in (i) the weight ratio of the source of an element $E_{SM2}$, calculated as element, to the source of an oxidic support, calculated as the oxide or mixed oxide of the element $E_{OS1}$ and the optional element $E_{OS2}$, is in the range of from 0.1 to 3 weight-%, more preferably in the range of from 0.2 to 1.0 weight-%, more preferably in the range of from 0.3 to 0.8 weight-%, more preferably in the range of from 0.4 to 0.6 weight-%.

It is preferred that preparing the mixture in (i) comprises stirring of the mixture for a period of time in the range of from 1 h to 10 d, more preferably of from 1 d to 7 d, more preferably of from 3 d to 6 d.

The process may comprise further process steps. It is preferred that the process further comprises after (i) and prior to (ii)

(a) optionally isolating the precursor of the catalytic material obtained in (i), preferably by filtration; and/or, preferably and (b) optionally washing the precursor of the catalytic material obtained in (i) or (a), preferably with deionized water; and/or, preferably and (c) optionally drying the impregnated catalytic material obtained in (i), (a), or (b) in a gas atmosphere.

In the case where the process comprises (c) drying the impregnated catalytic material obtained in (i), (a), or (b) in a gas atmosphere, it is preferred that drying in (c) is carried out at a temperature of the gas atmosphere in the range of from 30 to 80, more preferably in the range of from 50 to 70° C., more preferably in the range of from 55 to 65° C.

Further in the case where the process comprises (c) drying the impregnated catalytic material obtained in (i), (a), or (b) in a gas atmosphere, it is preferred that the gas atmosphere for drying comprises nitrogen, oxygen, or a mixture thereof, wherein the gas atmosphere is preferably oxygen, air, or lean air.

It is preferred that calcining the catalytic material in a gas atmosphere in (ii) is carried out at a temperature of the gas atmosphere in the range of from 300 to 700° C., preferably in the range of from 400 to 600° C., more preferably in the range of from 450 to 550° C.

It is preferred that the gas atmosphere for calcining in (ii) comprises nitrogen, oxygen, or a mixture thereof, wherein the gas atmosphere is preferably oxygen, air, or lean air.

Further, the present invention relates to a catalytic material obtainable and/or obtained by the process of any one of the embodiments disclosed herein.

Further, the present invention relates to a process for the preparation of one or more of 4,4'-methylenedianiline, 2,2'-methylenedianiline, 2,4'-methylenedianiline, and oligomers of two or more thereof, preferably for the preparation of 4,4'-methylenedianiline, 2,2'-methylenedianiline, and 2,4'-methylenedianiline, more preferably for the preparation of 4,4'-methylenedianiline, the process comprising (1) providing a reactor comprising a reaction zone, wherein the reaction zone comprises a catalytic material according to any one of the embodiments disclosed herein;

(2) providing a feed into the reaction zone according to (1), wherein the feed comprises one or more of aniline, formaldehyde, and N,N'-diphenylmethylenediamine;

(3) converting the feed under reaction conditions in the reaction zone; obtaining a product mixture comprising one or more of 4,4'-methylenedianiline, 2,2'-methylenedianiline, 2,4'-methylenedianiline, and oligomers of two or more thereof;

(4) separating the product mixture from the reaction zone.

It is preferred that the process is carried out in batch mode or in continuous mode.

It is preferred that the catalytic material is present in a fixed bed or in a fluidized bed.

It is preferred that the catalytic material is comprised in a molding.

It is preferred that the catalytic material is dried prior to (1) in a gas atmosphere, wherein the gas atmosphere has a temperature in the range of from 100 to 300° C., more preferably in the range of from 150 to 250° C., more preferably in the range of from 190 to 210° C. It is preferred that the gas atmosphere comprises one or more of nitrogen, oxygen, and a mixture thereof, wherein the gas atmosphere is preferably oxygen, air, or lean air. It is preferred that drying is performed for a duration in the range of from 10 to 40 h, more preferably in the range of from 20 to 30 h, more preferably in the range of from 23 to 25 h.

The process may comprise further process steps. It is preferred that the process further comprises after (1) and prior to (2)

(C) converting a mixture of aniline and formaldehyde to obtain a feed.

In the case where the process further comprises (C), it is preferred that the mixture for conversion in (C) comprises a molar ratio of aniline to formaldehyde in the mixture in the range of from 1.5:1 to 10.1:1, more preferably in the range of from 1.9:1 to 5.1:1, more preferably in the range of from 1.9:1 to 3.5:1.

Further in the case where the process further comprises (C), it is preferred that (C) comprises heating the mixture at a temperature in the range of from 20 to 80° C., more preferably in the range of from 40 to 60° C., more preferably in the range of from 45 to 55° C.

It is preferred that the reaction conditions in (3) comprise heating at a temperature in the range of from 100 to 200° C., more preferably in the range of from 130 to 170° C., more preferably in the range of from 145 to 155° C.

It is preferred that the reaction conditions in the reaction zone in (3) comprise a pressure of equal to or smaller than 100 bar, preferably of equal to or smaller than 90, more preferably of equal to or smaller than 70, more preferably of equal to or smaller than 50, more preferably of equal to or smaller than 30, and more preferably of equal to or smaller than 10 bars.

It is preferred that (3) is performed under a gas atmosphere, wherein the gas atmosphere in (3) preferably comprises one or more inert gases, more preferably nitrogen and/or argon, more preferably nitrogen.

As mentioned above, the process may comprise further process steps. It is preferred that the process further comprises after (4)

(5) separating the catalytic material from the reaction zone, preferably by filtration.

As mentioned above, the process may comprise further process steps. It is preferred that the process further comprises after (5)

(6) recycling the catalytic material to (1).

In the case where the process further comprises (5) and (6), it is preferred that after (5) and prior to (6) the catalytic material is not subject to a step of washing or drying, wherein preferably the catalytic material is not subject to any treatment after (5) and prior to (6).

In the case where the process further comprises (6) recycling of the catalytic material to (1), it is preferred that the process according to any one of the embodiments disclosed herein is performed n times, wherein n is a natural number equal or higher than 1, wherein n preferably ranges from 1 to 100, more preferably from 1 to more preferably from 1 to 50, more preferably from 1 to 20, more preferably from 1 to 10, and more preferably from 1 to 5. Therefore, it is preferred that the catalytic material is recycled after the process of any one of the embodiments is performed in (1) for performing the process of any one of the embodiments disclosed herein a further time.

Yet further, the present invention relates to a catalytic material according to any one of the embodiments disclosed herein in a process for the preparation of one or more of 4,4'-methylenedianiline, 2,2'-methylenedianiline, 2,4'-methylenedianiline, and oligomers of two or more thereof, preferably for the preparation of one or more of 4,4'-methylenedianiline, 2,2'-methylenedianiline, and 2,4'-methylenedianiline, more preferably for the preparation of 4,4'-methylenedianiline.

According to the present invention the Brønsted acidity and the Lewis acidity were determined using an IR-spectrometer, particularly employing a HV-FTIR-cell, wherein pyridine was used as probe gas. Preferably, a sample was pressed to a pellet. The measurement conditions preferably included heating of a sample in air to about 250° C. for about 1 h. Thus, water and any volatile substances could be removed from the sample. Further, the measurement conditions preferably included applying a low pressure ("high-vacuum" of about $10^{-5}$ mbar). Preferably, the sample cooled down to about 50° C. while applying the low pressure. The measurement was preferably conducted at about 150° C. for the entire duration of the measurement. Thus, the condensation of pyridine in the cell could be avoided. Accordingly, the controlled and complete exposition of the sample could be ensured.

The unit bar(abs) refers to an absolute pressure wherein 1 bar equals $10^5$ Pa.

The present invention is further illustrated by the following set of embodiments and combinations of embodiments resulting from the dependencies and back-references as indicated. In particular, it is noted that in each instance where a range of embodiments is mentioned, for example in the context of a term such as "The catalytic material of any one of embodiments 1 to 4", every embodiment in this range is meant to be explicitly disclosed for the skilled person, i.e. the wording of this term is to be understood by the skilled person as being synonymous to "The catalytic material of any one of embodiments 1, 2, 3, and 4". Further, it is explicitly noted that the following set of embodiments is not the set of claims determining the extent of protection, but represents a suitably structured part of the description directed to general and preferred aspects of the present invention.

1. A catalytic material for the preparation of one or more of 4,4'-methylenedianiline, 2,2'-methylenedianiline, 2,4'-methylenedianiline, and oligomers of two or more thereof, preferably of one or more of 4,4'-methylene-dianiline, 2,2'-methylenedianiline, and 2,4'-methylene-dianiline, more preferably for the preparation of 4,4'-methylenedianiline, the catalytic material comprising an oxidic support, wherein the oxidic support comprises an element $E_{OS1}$ selected from the group consisting of Ti, Zr, Al, Si, and mixtures of two or more thereof, and further comprising a supported material supported on the oxidic support, wherein the supported material comprises an element $E_{SM1}$ selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb, and mixtures of two or more thereof.

2. The catalytic material of embodiment 1, wherein $E_{OS1}$ is Al and/or Si, wherein preferably $E_{OS1}$ is Si.

3. The catalytic material of embodiment 1 or 2, wherein the oxidic support comprises, preferably consists of, titania, zirconia, alumina, or silica.

4. The catalytic material of any one of embodiments 1 to 3, wherein from 95 to 100 weight-% of the oxidic support consists of $E_{OS1}$, O, and H, preferably from 97 to 100 weight-%, more preferably from 98 to 100 weight-%, more preferably from 99 to 100 weight-%, based on the total weight of the oxidic support.

5. The catalytic material of any one of embodiments 1 to 3, wherein the oxidic support further comprises an element $E_{OS2}$ selected from group 4, 13 and 14 elements of the periodic system of elements, including mixtures of two or more thereof, wherein $E_{OS2}$ is different to $E_{OS1}$.

6. The catalytic material of embodiment 5, wherein $E_{OS2}$ is selected from the group consisting of Ti, Zr, Al, Si, Sn, and mixtures of two or more thereof, wherein $E_{OS2}$ preferably comprises Al and/or Si, wherein more preferably $E_{OS2}$ comprises Al, and wherein more preferably $E_{OS2}$ consists of Al.

7. The catalytic material of embodiment 5 or 6, wherein the oxidic support comprises, preferably consists of, silica-alumina, titania-silica, titania-alumina, zirconia-silica, zirconia-alumina, or titania-zirconia, wherein more preferably the oxidic support comprises, preferably consists of, silica-alumina.

8. The catalytic material of any of embodiments 5 to 7, wherein from 95 to 100 weight-% of the oxidic support consists of $E_{OS1}$, $E_{OS2}$, O, and H, preferably from 97 to 100 weight-%, more preferably from 98 to 100 weight-%, more preferably from 99 to 100 weight-%, based on the total weight of the oxidic support.

9. The catalytic material of any one of embodiments 1 to 8, wherein the oxidic support comprises, preferably consists of, a zeolitic material.

10. The catalytic material of embodiment 9, wherein the zeolitic material comprises $E_{OS1}$ and optionally $E_{OS2}$ in its framework structure, wherein $E_{OS1}$ more preferably is Si, and wherein $E_{OS2}$ more preferably is Al, wherein the zeolitic material more preferably comprises, preferably consists of, a 10-membered ring pore zeolitic material and/or a 12-membered ring pore zeolitic material.

11. The catalytic material of embodiment 10, wherein the zeolitic material comprises $E_{OS1}$ and $E_{OS2}$ in its framework structure, wherein $E_{OS1}$ more preferably is Si, and wherein $E_{OS2}$ more preferably is Al, wherein the zeolitic material exhibits a molar ratio of $E_{OS1}$ to $E_{OS2}$ in the range of from 5 to 50, preferably in the range of from 10 to 20, more preferably in the range of from 13 to 16.

12. The catalytic material of embodiment 10 or 11, wherein the 10-membered ring pore zeolitic material has a framework structure type selected from the group consisting of FER, TON, MTT, SZR, MFI, MWW, AEL, HEU, AFO, a mixture of two or more thereof and a mixed type of two or more thereof, preferably selected from the group consisting of FER, TON, MFI, MWW, AEL, HEU, AFO, a mixture of two or more thereof and a mixed type of two or more thereof, more preferably selected from the group consisting of MFI and MWW, wherein more preferably the 10-membered ring pore zeolitic material has a framework type MWW.

13. The catalytic material of any one of embodiments 10 to 12, wherein the 10-membered ring pore zeolitic material having a framework structure type MWW is selected from the group consisting of MCM-22, ERB-1, ITQ-1, PSH-3, and SSZ-25 and MCM-22, including mixtures of two or more thereof, wherein more preferably the 10-membered ring pore zeolitic material having a framework structure type MWW comprises MCM-22, wherein more preferably the 10-membered ring pore zeolitic material having a framework structure type MWW is MCM-22.

14. The catalytic material of any one of embodiments 10 to 13, wherein the 12-membered ring pore zeolitic material has a framework structure type selected from the group consisting of BEA, FAU, USY, GME, MOR, OFF, a mixture of two or more thereof and a mixed type of two or more thereof, preferably selected from the group consisting of BEA, USY, FAU, a mixture of two or more thereof and a mixed type of two or more thereof, wherein more preferably the 12-membered ring pore zeolitic material has a framework type FAU.

15. The catalytic material of embodiment 14, wherein the zeolitic material having a framework structure type FAU is selected from the group consisting of ZSM-3, Faujasite, [Al—Ge—O]-FAU, CSZ-1, ECR-30, Zeolite X, Zeolite Y, LZ-210, SAPO-37, ZSM-20, Na-X, US-Y, Na-Y, [Ga—Ge—O]-FAU, Li-LSX, [Ga—Al—Si—O]-FAU, and [Ga—Si—O]-FAU, including mixtures of two or more thereof, preferably from the group consisting of ZSM-3, Faujasite, CSZ-1, ECR-30, Zeolite X, Zeolite Y, LZ-210, ZSM-20, Na-X, US-Y, Na-Y, and Li-LSX, including mixtures of two or more thereof, more preferably from the group consisting of Faujasite, Zeolite X, Zeolite Y, Na-X, US-Y, and Na-Y, including mixtures of two or more thereof, more preferably from the group consisting of Faujasite, Zeolite X, and Zeolite Y, including mixtures of two or more thereof, wherein more preferably the zeolitic material having a framework structure type FAU comprises, more preferably consists of, zeolite X and/or zeolite Y, preferably zeolite Y.

16. The catalytic material of any one of embodiments 1 to 15, wherein $E_{SM1}$ is selected from the group consisting of Sc, Y, La, Ce, Nd, Pr, Hf, Cr, Fe, Co, Ni, Cu, Zn, Pb, Zr, and mixtures of two or more thereof, preferably from the group consisting of Sc, La, Ce, Hf, Cr, Fe, Ni, Cu, Zn, Zr, and mixtures of two or more thereof, more preferably from the group consisting of Sc, La, Ce, Hf, Fe, Zn, Zr, and mixtures of two or more thereof, more preferably from the group consisting of Sc, Hf, Fe, Zn, Zr, and mixtures of two or more thereof, and mixtures of two or more thereof, wherein more preferably $E_{SM1}$ is Hf and/or Fe, wherein more preferably $E_{SM1}$ is Hf.

17. The catalytic material of any one of embodiments 1 to 16, wherein the catalytic material comprises $E_{SM1}$, calculated as element, in an amount in the range of from 0.1 to 10 weight-%, preferably in the range of from 1 to 5 weight-%, more preferably in the range of from 1.1 to 4.9 weight-%, more preferably in the range of from 1.2 to 4.5 weight-%, more preferably in the range of from 2.0 to 4.0 weight-%, more preferably in the range of from 2.5 to 3.5 weight-%, based on the total weight of the oxidic support, preferably determined according to Reference Example 8.

18. The catalytic material of any one of embodiments 1 to 17, wherein from 95 to 100 weight-% of the supported material consists of $E_{SM1}$, O and H, preferably from 97 to 100 weight-%, more preferably from 98 to 100 weight-%, more preferably from 99 to 100 weight-%, based on the total weight of the oxidic support.

19. The catalytic material of any one of embodiments 1 to 18, wherein the supported material further comprises an element $E_{SM2}$ selected from groups 3-14 of the periodic system of elements, rare earth metals, and mixtures of two or more thereof, wherein $E_{SM2}$ is different to $E_{SM1}$.

20. The catalytic material of embodiment 19, wherein $E_{SM2}$ is selected from groups 3, 4, 5, 6, 8, 10, 11, 12, 14, rare earth metals, and mixtures of two or more thereof, preferably from the group consisting of Sc, Y, La, Ce, Nd, Pr, Ti, Zr, Hf, V, Nb, Ta, Cr, Mo, W, Fe, Co, Ni, Cu, Zn, Ge, Sn, Pb, and mixtures of two or more thereof, more preferably from the group consisting of Sc, La, Ce, Zr, Hf, Nb, Ta, Cr, Fe, Ni, Cu, Zn, Sn, and mixtures of two or more thereof, more preferably from the group consisting of Sc, La, Ce, Zr, Hf, Nb, Ta, Fe, Zn, Sn, and mixtures of two or more thereof, more preferably from the group consisting of Sc, Zr, Hf, Nb, Fe, Zn, Sn, and mixtures of two or more thereof, more preferably from the group consisting of Sc, Zr, Hf, Nb, Fe, Zn, and mixtures of two or more thereof, wherein more preferably $E_{SM2}$ is Zn.

21. The catalytic material of embodiment 19 or 20, wherein the catalytic material comprises $E_{SM2}$, calculated as element, in an amount in the range of from 0.1 to 3 weight-%, preferably in the range of from 0.2 to 1.0 weight-%, more preferably in the range of from 0.3 to 0.8 weight-%, more preferably in the range of from 0.4 to 0.6 weight-%, based on the total weight of the oxidic support, preferably determined according to Reference Example 8.

22. The catalytic material of any one of embodiments 19 to 21, wherein from 95 to 100 weight-% of the supported material consists of $E_{SM1}$, $E_{SM2}$, O, and H, preferably from 97 to 100 weight-%, more preferably from 98 to 100 weight-%, more preferably from 99 to 100 weight-%, based on the total weight of the supported material.

23. The catalytic material of any one of embodiments 1 to 22, wherein from 95 to 100 weight-% of the catalytic material consists of the oxidic support and the supported material, preferably from 97 to 100 weight-%, more preferably from 98 to 100 weight-%, more preferably from 99 to 100 weight-%, based on the total weight of the catalytic material.

24. The catalytic material of any one of embodiments 1 to 23, exhibiting a type IV nitrogen adsorption/desorption isotherm, wherein the nitrogen adsorption/desorption isotherm is preferably determined according to Reference Example 3.

25. The catalytic material of any one of embodiments 1 to 24, having a total pore volume in the range of from 0.5 to 1.0 cm$^3$/g, preferably in the range of from 0.65 to 0.80 cm$^3$/g, more preferably in the range of from 0.70 to 0.76 cm$^3$/g, more preferably in the range of from 0.72 to 0.74 cm$^3$/g, wherein the total pore volume is preferably determined according to Reference Example 4.

26. The catalytic material of any one of embodiments 1 to 25, having a mesopore volume $V_{meso}$ in the range of from 0.50 to 1.30 cm$^3$/g, preferably in the range of from 0.60 to 1.20 cm$^3$/g, more preferably in the range of from 0.70 to 1.10 cm$^3$/g, more preferably in the range of from 0.80 to 1.00 cm$^3$/g, wherein the mesopore volume is preferably determined according to Reference Example 5.

27. The catalytic material of any one of embodiments 1 to 26, having a BET specific surface area $S_{BET}$ in the range of from 100 to 400 m$^2$/g, preferably in the range of from 150 to 350 m$^2$/g, more preferably in the range of from 160 to 330 m$^2$/g, more preferably in the range of from 170 to 310 m$^2$/g, wherein the BET specific surface area $S_{BET}$ is preferably determined according to Reference Example 6.

28. The catalytic material of any one of embodiments 1 to 27, having a specific external surface area $S_{EXT}$ in the range of from 90 to 390 m$^2$/g, preferably in the range of from 140 to 340 m$^2$/g, more preferably in the range of from 150 to 320 m$^2$/g, more preferably in the range of from 160 to 300 m$^2$/g, wherein the specific external surface $S_{EXT}$ area is preferably determined according to Reference Example 6.

29. The catalytic material of any one of embodiments 1 to 28, showing in the temperature programmed desorption of ammonia (NH$_3$-TPD) a first desorption peak having a maximum in the range of from 150 to 250° C., preferably in the range of from 170 to 230° C., wherein the temperature programmed desorption of ammonia (NH$_3$-TPD) is preferably determined according to Reference Example 7.

30. The catalytic material of any one of embodiments 1 to 29, showing in the temperature programmed desorption of ammonia (NH$_3$-TPD) a second desorption peak having a maximum in the range of from 275 to 400° C., preferably in the range of from 300 to 375° C., wherein the temperature programmed desorption of ammonia (NH$_3$-TPD) is preferably determined according to Reference Example 7.

31. The catalytic material of any one of embodiments 1 to 30, exhibiting an acid site density in the range of from 0.050 to 1.000 μmol/g, preferably in the range of from 0.100 to 0.750, more preferably in the range of from 0.150 to 0.600 μmol/g, more preferably in the range of from 0.157 to 0.550 μmol/g, preferably determined as described in Reference Example 7.

32. The catalytic material of any one of embodiments 1 to 31, exhibiting a Brønstedt acid site density of equal or less than 100 μmol/g, preferably equal or less than 75 μmol/g, more preferably equal or less than 65 μmol/g, preferably determined as described in Reference Example 1.

33. The catalytic material of any one of embodiments 1 to 32, exhibiting a Lewis acid site density in the range of from 10 to 150 μmol/g, preferably in the range of from 25 to 130, more preferably in the range of from 40 to 100 μmol/g, more preferably in the range of from 50 to 75 μmol/g, more preferably in the range of from 60 to 65 μmol/g, preferably determined as described in Reference Example 1.

34. The catalytic material of any one of embodiments 1 to 33, exhibiting a selectivity towards one or more of 4,4'-methylenedianiline, 2,2'-methylenedianiline, 2,4'-methylenedianiline, and oligomers of two or more thereof, preferably towards one or more of 4,4'-methylenedianiline, 2,2'-methylenedianiline, and 2,4'-methylenedianiline, in the range of from 4 to 100%, preferably in the range of from 30 to 90%, more preferably in the range of from 45 to 75%, preferably determined as described in Example 4.

35. The catalytic material of embodiment 34, exhibiting a molar isomer ratio of 4,4'-methylenedianiline to 2,2'-methylenedianiline and 2,4'-methylenedianiline in the range of from 0.1 to 20, preferably in the range of from 0.5 to 15, more preferably in the range of from 1.0 to 10, more preferably in the range of from 2.0 to 5.0, preferably in the range of from 3.5 to 4.5, preferably determined as described in Example 4.

36. A process for the preparation of a catalytic material, preferably for the preparation of a catalytic material according to any one of embodiments 1 to 35, the process comprising (i) preparing a mixture comprising a liquid solvent system, a source of an oxidic support comprising an element $E_{OS1}$ selected from the group consisting of Ti, Zr, Al, Si, and mixtures of two or more thereof, a source of an element $E_{SM1}$ selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb, and mixtures of two or more thereof, and optionally a source of an element $E_{SM2}$ selected from groups 3-14 of the periodic system of elements, rare earth metals, and mixtures of two or more thereof, wherein the optional $E_{SM2}$ is different to $E_{SM1}$, obtaining a precursor of the catalytic material;

(ii) calcining the precursor of the catalytic material in a gas atmosphere, obtaining the catalytic material.

37. The process of embodiment 36, wherein preparing a mixture in (i) is carried out at a temperature in the range of from 10 to 35° C., preferably in the range of from 15 to 30° C., more preferably in the range of from 20 to 25° C.

38. The process of embodiment 36 or 37, wherein the liquid solvent system comprises one or more of water, deionized water, ultrapure water, methanol, ethanol, isopropanol, tetrahydrofuran, and acetic acid, preferably ultrapure water.

39. The process of any one of embodiments 36 to 38, wherein $E_{OS1}$ comprises Al and/or Si, preferably comprises Si, wherein more preferably $E_{OS1}$ consists of Si.

40. The process of any one of embodiments 36 to 39, wherein the source of an oxidic support further comprises an element $E_{OS2}$ selected from group 4, 13 and 14 elements of the periodic system of elements, including mixtures of two or more thereof, wherein $E_{OS2}$ is different to $E_{OS1}$.

41. The process of embodiment 40, wherein $E_{OS2}$ is selected from the group consisting of Ti, Zr, Al, Si, Sn, and mixtures of two or more thereof, wherein $E_{OS2}$ preferably comprises Al and/or Si, wherein more preferably $E_{OS2}$ comprises Al, and wherein more preferably $E_{OS2}$ consists of Al.

42. The process of any one of embodiments 36 to 41, wherein the source of an oxidic support comprises one or more of silica, alumina, titania, zirconia, silica-alumina, titania-silica, titania-alumina, zirconia-silica, zirconia-alumina, titania-zirconia, preferably one or more of silica, alumina, silica-alumina, wherein more preferably the source of an oxidic support comprises silica-alumina.

43. The process of any one of embodiments 36 to 42, wherein the source of an oxidic support comprises a zeolitic material.

44. The process of embodiment 43, wherein the zeolitic material comprises $E_{OS1}$ and optionally $E_{OS2}$ in its framework structure, wherein $E_{OS1}$ more preferably is Si, and wherein $E_{OS2}$ more preferably is Al, wherein the zeolitic material more preferably comprises, preferably consists of, a 10-membered ring pore zeolitic material and/or a 12-membered ring pore zeolitic material.

45. The process of embodiment 44, wherein the zeolitic material comprises $E_{OS1}$ and $E_{OS2}$ in its framework structure, wherein $E_{OS1}$ more preferably is Si, and wherein $E_{OS2}$ more preferably is Al, wherein the zeolitic material exhibits a molar ratio of $E_{OS1}$ to $E_{OS2}$ in the range of from 5 to 50, preferably in the range of from 10 to 20, more preferably in the range of from 13 to 16.

46. The process of embodiment 44 or 45, wherein the 10-membered ring pore zeolitic material has a framework structure type selected from the group consisting of FER, TON, MTT, SZR, MFI, MWW, AEL, HEU, AFO, a mixture of two or more thereof and a mixed type of two or more thereof, preferably selected from the group consisting of FER, TON, MFI, MWW, AEL, HEU, AFO, a mixture of two or more thereof and a mixed type of two or more thereof, more preferably selected from the group consisting of MFI and MWW, wherein more preferably the 10-membered ring pore zeolitic material has a framework type MWW.

47. The process of any one of embodiments 44 to 46, wherein the 10-membered ring pore zeolitic material having a framework structure type MWW is selected from the group consisting of MCM-22, ERB-1, ITQ-1, PSH-3, and SSZ-25 and MCM-22, including mixtures of two or more thereof, wherein more preferably the 10-membered ring pore zeolitic material having a framework structure type MWW comprises MCM-22, wherein more preferably the 10-membered ring pore zeolitic material having a framework structure type MWW is MCM-22.

48. The process of any one of embodiments 44 to 47, wherein the 12-membered ring pore zeolitic material has a framework structure type selected from the group consisting of BEA, FAU, USY, GME, MOR, OFF, a mixture of two or more thereof and a mixed type of two or more thereof, preferably selected from the group consisting of BEA, USY, FAU, a mixture of two or more thereof and a mixed type of two or more thereof, wherein more preferably the 12-membered ring pore zeolitic material has a framework type FAU.

49. The process of embodiment 48, wherein the zeolitic material having a framework structure type FAU is selected from the group consisting of ZSM-3, Faujasite, [Al—Ge—O]-FAU, CSZ-1, ECR-30, Zeolite X, Zeolite Y, LZ-210, SAPO-37, ZSM-20, Na-X, US-Y, Na-Y, [Ga—Ge—O]-FAU, Li-LSX, [Ga—Al—Si—O]-FAU, and [Ga—Si—O]-FAU, including mixtures of two or more thereof, preferably from the group consisting of ZSM-3, Faujasite, CSZ-1, ECR-30, Zeolite X, Zeolite Y, LZ-210, ZSM-20, Na-X, US-Y, Na-Y, and Li-LSX, including mixtures of two or more thereof, more preferably from the group consisting of Faujasite, Zeolite X, Zeolite Y, Na-X, US-Y, and Na-Y, including mixtures of two or more thereof, more preferably from the group consisting of Faujasite, Zeolite X, and Zeolite Y, including mixtures of two or more thereof, wherein more preferably the zeolitic material having a framework structure type FAU comprises, more preferably consists of, zeolite X and/or zeolite Y, preferably zeolite Y.

50. The process of any one of embodiments 36 to 49, wherein the source of the element $E_{SM1}$ is a salt, wherein the salt preferably comprises one or more of a halide, a nitrate, an acetate, a sulfate, a phosphate, and a carbonate, more preferably one or more of a fluoride, a chloride, a bromide, and an iodide, more preferably the source of the element $E_{SM1}$ comprises a chloride, preferably the source of the element $E_{SM1}$ consists of a chloride.

51. The process of any one of embodiments 36 to 50, wherein $E_{SM1}$ is selected from the group consisting of Sc, Y, La, Ce, Nd, Pr, Hf, Cr, Fe, Co, Ni, Cu, Zn, Pb, Zr, and mixtures of two or more thereof, preferably from the group consisting of Sc, La, Ce, Hf, Cr, Fe, Ni, Cu, Zn, Zr and mixtures of two or more thereof, more preferably from the group consisting of Sc, La, Ce, Hf, Fe, Zn, Zr, and mixtures of two or more thereof, more preferably from the group consisting of Sc, Hf, Fe, Zn, Zr, and mixtures of two or more thereof, wherein more preferably $E_{SM1}$ is Fe and/or Hf, wherein more preferably $E_{SM1}$ is Hf.

52. The process of any one of embodiments 36 to 51, wherein the mixture prepared in (i) comprises the source of an element $E_{SM2}$, wherein $E_{SM2}$ is different to $E_{SM1}$.

53. The process of any one of embodiments 36 to 52, wherein $E_{SM2}$ is selected from groups 3, 4, 5, 6, 8, 10, 11, 12, 14, and rare earth metals, and mixtures of two or more thereof, preferably from the group consisting of Sc, Y, La, Ce, Nd, Pr, Ti, Zr, Hf, V, Nb, Ta, Cr, Mo, W, Fe, Co, Ni, Cu, Zn, Ge, Sn, Pb, and mixtures of two or more thereof, more preferably from the group consisting of Sc, La, Ce, Zr, Hf, Nb, Ta, Cr, Fe, Ni, Cu, Zn, Sn, and mixtures of two or more thereof, more preferably from the group consisting of Sc, La, Ce, Zr, Hf, Nb, Ta, Fe, Zn, Sn, and mixtures of two or more thereof, more preferably from the group consisting of Sc, Zr, Hf, Nb, Fe, Zn, Sn, and mixtures of two or more thereof, more preferably from the group consisting of Sc, Zr, Hf, Nb, Fe, Zn, and mixtures of two or more thereof, wherein more preferably $E_{SM2}$ is Zn.

54. The process of any one of embodiments 36 to 53, wherein in the mixture prepared in (i) the weight ratio of the source of an element $E_{SM1}$, calculated as element, to the source of an oxidic support, calculated as the oxide or mixed oxide of the element $E_{OS1}$ and the optional element $E_{OS2}$, is in the range of from 0.1 to 10 weight-%, preferably in the range of from 1 to 5 weight-%, more preferably in the range of from 1.1 to 4.9 weight-%, more preferably in the range of from 1.2 to 4.5 weight-%, more preferably in the range of from 2.0 to 4.0 weight-%, more preferably in the range of from 2.5 to 3.5 weight-%.

55. The process of any one of embodiments 36 to 54, wherein in the mixture prepared in (i) the weight ratio of the source of an element $E_{SM2}$, calculated as element, to the source of an oxidic support, calculated as the oxide or mixed oxide of the element $E_{OS1}$ and the optional element $E_{OS2}$, is in the range of from 0.1 to 3 weight-%, preferably in the range of from 0.2 to 1.0 weight-%, more preferably in the range of from 0.3 to 0.8 weight-%, more preferably in the range of from 0.4 to 0.6 weight-%.

56. The process of any one of embodiments 36 to 55, wherein preparing the mixture in (i) comprises stirring of the mixture for a period of time in the range of from 1 h to 10 d, preferably of from 1 d to 7 d, more preferably of from 3 d to 6 d.

57. The process of any one of embodiments 36 to 56, wherein after (i) and prior to (ii) the process further comprises
   (a) optionally isolating the precursor of the catalytic material obtained in (i), preferably by filtration; and/or, preferably and
   (b) optionally washing the precursor of the catalytic material obtained in (i) or (a), preferably with deionized water; and/or, preferably and
   (c) optionally drying the impregnated catalytic material obtained in (i), (a), or (b) in a gas atmosphere.

58. The process of embodiment 57, wherein drying in (c) is carried out at a temperature of the gas atmosphere in the range of from 30 to 80, preferably in the range of from 50 to 70° C., more preferably in the range of from 55 to 65° C.

59. The process of embodiment 57 or 58, wherein the gas atmosphere for drying comprises nitrogen, oxygen, or a mixture thereof, wherein the gas atmosphere is preferably oxygen, air, or lean air.

60. The process of any one of embodiments 36 to 59, wherein calcining the catalytic material in a gas atmosphere in (ii) is carried out at a temperature of the gas atmosphere in the range of from 300 to 700° C., preferably in the range of from 400 to 600° C., more preferably in the range of from 450 to 550° C.

61. The process of any one of embodiments 36 to 60, wherein the gas atmosphere for calcining in (ii) comprises nitrogen, oxygen, or a mixture thereof, wherein the gas atmosphere is preferably oxygen, air, or lean air.

62. A catalytic material obtainable and/or obtained by the process of any one of embodiments 36 to 61.

63. A process for the preparation of one or more of 4,4'-methylenedianiline, 2,2'-methylenedianiline, 2,4'-methylenedianiline, and oligomers of two or more thereof, preferably for the preparation of 4,4'-methylenedianiline, 2,2'-methylenedianiline, and 2,4'-methylenedianiline, more preferably for the preparation of 4,4'-methylenedianiline, the process comprising
   (1) providing a reactor comprising a reaction zone, wherein the reaction zone comprises a catalytic material according to any one of embodiments 1 to 35 and 62;
   (2) providing a feed into the reaction zone according to (1), wherein the feed comprises one or more of aniline, formaldehyde, and N,N'-diphenylmethylenediamine;
   (3) converting the feed under reaction conditions in the reaction zone; obtaining a product mixture comprising one or more of 4,4'-methylenedianiline, 2,2'-methylenedianiline, 2,4'-methylenedianiline, and oligomers of two or more thereof;
   (4) separating the product mixture from the reaction zone.

64. The process of embodiment 63, wherein the process is carried out in batch mode or in continuous mode.

65. The process of embodiment 63 or 64, wherein the catalytic material is present in a fixed bed or in a fluidized bed.

66. The process of any one of embodiments 63 to 65, wherein the catalytic material is comprised in a molding.

67. The process of any one of embodiments 63 to 66, wherein the catalytic material is dried prior to (1) in a gas atmosphere, wherein the gas atmosphere has a temperature in the range of from 100 to 300° C., preferably in the range of from 150 to 250° C., more preferably in the range of from 190 to 210° C.

68. The process of embodiment 67, wherein the gas atmosphere comprises one or more of nitrogen, oxygen, and a mixture thereof, wherein the gas atmosphere is preferably oxygen, air, or lean air.

69. The process of embodiment 67 or 68, wherein the drying is performed for a duration in the range of from 10 to 40 h, preferably in the range of from 20 to 30 h, more preferably in the range of from 23 to 25 h.

70. The process of any one of embodiments 63 to 69, further comprising after (1) and prior to (2)
    (C) converting a mixture of aniline and formaldehyde to obtain a feed.

71. The process of embodiment 70, wherein the mixture for conversion in (C) comprises a molar ratio of aniline to formaldehyde in the mixture in the range of from 1.5:1 to 10.1:1, preferably in the range of from 1.9:1 to 5.1:1, more preferably in the range of from 1.9:1 to 3.5:1.

72. The process of embodiment 70 or 71, wherein (C) comprises heating the mixture at a temperature in the range of from 20 to 80° C., preferably in the range of from 40 to 60° C., more preferably in the range of from 45 to 55° C.

73. The process of any one of embodiments 63 to 72, wherein the reaction conditions in (3) comprise heating at a temperature in the range of from 100 to 200° C., preferably in the range of from 130 to 170° C., more preferably in the range of from 145 to 155° C.

74. The process of any one of embodiments 63 to 73, wherein the reaction conditions in the reaction zone in (3) comprise a pressure of equal to or smaller than 100 bar, preferably of equal to or smaller than 90, more preferably of equal to or smaller than 70, more preferably of equal to or smaller than 50, more preferably of equal to or smaller than 30, and more preferably of equal to or smaller than 10 bars.

75. The process of any one of embodiments 63 to 74, wherein (3) is performed under a gas atmosphere, wherein the gas atmosphere in (3) preferably comprises one or more inert gases, preferably nitrogen and/or argon, more preferably nitrogen.

76. The process of any one of embodiments 63 to 75, further comprising after (4)
    (5) separating the catalytic material from the reaction zone, preferably by filtration.

77. The process of embodiment 76, further comprising after (5)
    (6) recycling the catalytic material to (1).

78. The process of embodiment 77, wherein after (5) and prior to (6) the catalytic material is not subject to a step of washing or drying, wherein preferably the catalytic material is not subject to any treatment after (5) and prior to (6).

79. The process of embodiment 78, wherein the process according to any one of the embodiments 63 to 78 is repeated n times, wherein n is a natural number equal or higher than 1, wherein n preferably ranges from 1 to 100, more preferably from 1 to more preferably from 1 to 50, more preferably from 1 to 20, more preferably from 1 to 10, and more preferably from 1 to 5.

80. Use of a catalytic material according to any one of embodiments 1 to 35 and embodiment 62 in a process for the preparation of one or more of 4,4'-methylene-dianiline, 2,2'-methylenedianiline, 2,4'-methylenedi-aniline, and oligomers of two or more thereof, preferably for the preparation of one or more of 4,4'-methylenedianiline, 2,2'-methylenedianiline, and 2,4'-methylenedianiline, more preferably for the preparation of 4,4'-methylenedianiline.

The present invention is further illustrated by the following Examples and Reference Examples.

EXAMPLES

Reference Example 1: Determination of the Lewis Acidity and of the Brønsted Acidity The nature of the acid sites and the acid site density were determined for a sample material by pyridine adsorption using FTIR spectroscopy with pyridine as probe molecule. A self-supported wafer was placed in a cell under vacuum and activated at 250° C. for 1 h. The cell was subsequently cooled and a reference spectrum was recorded at 150° C. After this, the cell was further cooled and pyridine (25 mbar) was contacted with the wafer at 50° C. until the sample material was saturated. Weakly coordinated pyridine was removed by evacuation for 30 min, prior to IR spectrum recording at 150° C.

The difference IR spectra of adsorbed pyridine were measured for a sample and normalized to 10 mg of sample/cm². From the difference IR spectra bands assigned to pyridine adsorbed on hydroxyl groups or physisorbed pyridine at 1595 and 1445 cm$^{-1}$ were absent after evacuating the samples at 423 K, allowing for the quantification of Brønsted and Lewis acid sites, these were determined using Emeis' integrated molar extinction coefficients (see C. A. Emeis: "Determination of integrated molar extinction coefficients for infrared absorption bands of pyridine adsorbed on solid acid catalysts" in Journal of Catalysis 1993, vol. 141, p. 347-354 and M. Velthoen et al. "Probing acid sites in solid catalysts with pyridine UV-Vis spectroscopy" in Physical Chemistry Chemical Physics 2018, vol. 20, p. 21647-21659 as regards the determination of acidity properties of a material via spectroscopy and the interpretation of the resulting data) and the areas of the absorption bands at 1545 cm$^{-1}$ (Brønsted acid sites) and 1450 cm$^{-1}$ (Lewis acid sites).

Reference Example 2: Determination of the Thermogravimetric Profiles (TGA-MS) and Aniline-Sample Interaction A stock solution of aniline in THF was prepared (0.0025 g$_{Aniline}$/mL$_{THF}$) Catalyst samples were dried at 200° C. overnight. Then, 5 weight-% aniline with respect to the dry catalyst was added to the dry catalyst using the stock solution. The mixture was sealed and stirred at room temperature until dry (so called "free-flowing"). A sample was analyzed with TGA-MS, wherein TGA-MS measurements were carried out at a heating rate of 5° C./min to a final temperature of 600° C. under a nitrogen atmosphere.

As can be taken from the results shown in FIG. 1, the TGA-MS results indicate that the aniline-catalyst interaction is strongest in zeolite Y and weakest in non-loaded silica since the maximum MS intensity is reached for SiO$_2$, and inventive catalytic materials Hf, Zn/SiO$_2$ and Hf/SiO$_2$ at a temperature of about 100° C. whereas the maximum MS intensity is reached for zeolite Y at a temperature in the range of from 350 to 400° C.

Reference Example 3: Determination of $N_2$ Adsorption/Desorption Isotherm $N_2$ physisorption isotherms were collected at 77 K on a Micromeritics 3Flex Surface Characterization Analyzer. Samples were outgassed under vacuum at 423 K for 4 h prior to data collection.

Reference Example 4: Determination of the Total Pore Volume

The total pore volume was estimated by DFT calculations (0.731 cm$^3$/g for Hf Zn/SiO$_2$).

Reference Example 5: Determination of the Mesopore Volume

The mesopore volume $V_{meso}$ was determined via BJH method.

Reference Example 6: Determination of the BET Specific Surface Area $S_{BET}$ and of the Specific External Surface Area $S_{EXT}$ The specific surface area ($S_{BET}$) was determined using the BET method (0.001-0.20 p/p$_0$ range) and the specific external surface area ($S_{EXT}$) was obtained using the t-plot method.

Reference Example 7: Determination of Acidity with NH$_3$-TPD

The acidity of a catalytic material was measured by temperature-programmed-desorption of NH$_3$ (NH$_3$-TPD), which was conducted on a Gasmet DX4000 FTIR gas analyser with Calcmet software for converting the collected spectral data into ammonia concentrations. The sample was activated at 200° C. for 2 h under nitrogen, then cooled to 100° C. and dosed with an ammonia/nitrogen gas mixture until saturation at this temperature. Non-adsorbed ammonia was then flushed away with nitrogen at 100° C. The sample was subsequently heated at a linear heating rate under nitrogen and the amount of desorbed ammonia was monitored with a downstream detector.

Reference Example 8: Determination of Metal Content

Inductively coupled plasma-optical emission spectrometry (ICP-OES) was used to determine the metal content of the samples using a Varian 720-ES.

Example 1: Preparation of a Catalytic Material Comprising Hf and Zn Supported on Silica 0.542 g hafnium chloride (HfCl$_4$), 0.231 g zinc nitrate (Zn(NO$_3$)$_2$·6H$_2$O) and 10.090 g fumed silica (Cabot CAB-O-SIL M5) were added to 100 ml ultrapure water (Ultrapure water, Millipore Milli-Q Type 1) at around 23° C. The mixture had a theoretical content of 3.0 weight-% Hf and 0.5 weight-% Zn, each with respect to the total weight of the fumed silica. The mixture was covered with filter paper (Whatman Grade 5 2.5 μm), stirred for 5 days at around 23° C., and subsequently dried at 60° C. The dried material was then heated at a rate of 2° C./min to 500° C. and held at this temperature for 2 h.

The nature of the acid sites and the acid site density of the resulting material were determined by pyridine adsorption using FTIR spectroscopy with pyridine as probe molecule. No Brønsted acid sites were observed but 62.4 μmol/g of Lewis acid sites, both determined according to Reference Example 1. Independently thereof, the Lewis acidity was determined by temperature-programmed-desorption of ammonia according to Reference Example 7 as being 0.157 mmol/g. The material had a total pore volume of 0.731 cm$^3$/g, determined according to Reference Example 4, a BET specific surface area $S_{BET}$ of 176 m$^2$/g, a specific external surface area $S_{EXT}$ of 169 m$^2$/g, both determined according to Reference Example 6, and it showed a desorption peak having a maximum at about 225° C. in the temperature programmed desorption of ammonia (NH$_3$-TPD), determined according to Reference Example 7 disclosed herein. The specific surface area ($S_{BET}$) and the specific external surface area ($S_{EXT}$) were similar, indicating that the material was mesoporous. Thus, the mesopore volume was determined according to Reference Example 5 as being 0.97 cm$^3$/g. Furthermore, the metal contents were determined according to Reference Example 8 as being 2.7 weight-% Hf and 0.5 weight-% Zn, each based on 100 weight-% SiO$_2$.

Example 2: Preparation of a Catalytic Material Comprising Hf and Zn Supported on Silica-Alumina Example 1 was repeated wherein 112 mg hafnium chloride (HfCl$_4$), 50 mg zinc nitrate (Zn(NO$_3$)$_2$·6H$_2$O were used and 2039 mg silica-alumina (Grace, MS 13/110, 13% Al$_2$O$_3$, $S_{BET}$=475 m$^2$/g) were used instead of fumed silica as oxidic support.

The nature of the acid sites and the acid site density of the resulting material were determined by pyridine adsorption using FTIR spectroscopy with pyridine as probe molecule. 21.6 μmol/g of Brønsted acid sites were observed and 62.2 μmol/g of Lewis acid sites, both determined according to Reference Example 1. The Lewis acidity was also determined by temperature-programmed-desorption of ammonia according to Reference Example 7 as being 0.456 mmol/g. The material had a BET specific surface area $S_{BET}$ of 303 m$^2$/g, a specific external surface area SEXT of 294 m$^2$/g, both determined according to Reference Example 6, and it showed a desorption peak having a first maximum at about 190° C. and a second maximum at about 325° C. in the temperature programmed desorption of ammonia (NH$_3$-TPD), determined according to Reference Example 7 disclosed herein. The specific surface area ($S_{BET}$) and the specific external surface area ($S_{EXT}$) were similar, indicating that the material was mesoporous. Thus, the mesopore volume was determined according to Reference Example 5 as being 0.94 cm$^3$/g. Furthermore, the metal contents were determined according to Reference Example 8 as being 2.9 weight-% Hf and 0.5 weight-% Zn, each based on 100 weight-% SiO$_2$·Al$_2$O$_3$.

Example 3: Preparation of a Catalytic Material Comprising Fe Supported on Silica-Alumina Example 1 was repeated wherein 218 mg iron nitrate (Fe(NO$_3$)$_3$·9H$_2$O) were used instead of hafnium chloride and zinc nitrate, wherein further 984 mg silica-alumina (Grace, MS 13/110, 13% Al$_2$O$_3$, $S_{BET}$=475 m$^2$/g) has been used instead of silica as oxidic support. The mixture had a theoretical content of 3 weight-% Fe with respect to the total weight of the fumed silica-alumina.

The nature of the acid sites and the acid site density were determined by pyridine adsorption using FTIR spectroscopy with pyridine as probe molecule. 63.8 μmol/g of Brønsted acid sites were observed and 127.2 μmol/g of Lewis acid sites, both determined according to Reference Example 1. The Lewis acidity was also determined by temperature-programmed-desorption of ammonia according to Reference Example 7 as being 0.505 mmol/g. The material had a BET specific surface area $S_{BET}$ of 299 m$^2$/g, a specific external surface area $S_{EXT}$ of 284 m$^2$/g, both determined according to Reference Example 6, and it showed a desorption peak having a first maximum at about 180° C. and a second maximum at about 350° C. in the temperature programmed desorption of ammonia (NH$_3$-TPD), determined according to Reference Example 7 disclosed herein. The specific surface area ($S_{BET}$) and the specific external surface area ($S_{EXT}$) were similar, indicating that the material was mesoporous. Thus, the mesopore volume was determined according to Reference Example 5 as being 0.80 cm$^3$/g. Furthermore, the metal contents were determined according to Reference Example 8 as being 3.2 weight-% Fe, based on 100 weight-% SiO$_2$·Al$_2$O$_3$.

Example 4: Preparation of 4,4'-methylenedianiline, 2,2'-methylenedianiline, and 2,4'-methylenedianiline by Conversion of Aniline and Formaldehyde 155.0 mg of a catalytic material was dried overnight at 200° C. to afford 146.9 mg of a dried catalytic material.

0.32 mm internal diameter) and a flame ionisation detector maintained at 330° C. Samples of 1 μL were injected automatically with an AOC-20s autosampler and AOC-20i auto-injector. An injection temperature of 320° C., a 1:30 split ratio, and N$_2$ as carrier gas at a linear velocity of 24.7 cm/s were used. The initial temperature of the column was 50° C.; then it was increased at 15° C./min to 210° C. and kept for 25 min. Subsequently, the column was heated at 20° C./min to 320° C. and maintained at that temperature for 20 min. Compounds were identified with GC-MS and/or with comparing retention times of known compounds. Nitrobenzene was used as an external standard.

The isomer ratio was calculated according to the following formula:

$$\text{isomer ratio} = \text{peak area of 4,4'-methylenedianiline}/ \\ (\text{peak area of 2,2'-methylenedianiline} + \text{peak area} \\ \text{of 2,4'-methylenedianiline}).$$

For comparative reasons, the same catalyst testing has been carried out using a conventional MCM-22 (H-MCM-22, from China Catalyst Group with Si/Al=14), a conventional zeolite Y (CBV-720, from Zeolyst International with Si/Al=15), as well as silica supporting hafnium and zinc prepared in accordance with Example 1, and silica-alumina supporting hafnium and zinc prepared in accordance with Example 2.

TABLE 1

Results of the catalyzed preparation of 4,4'-methylenedianiline (also abbreviated as 4,4' or 4,4'-MDA), 2,2'-methylenedianiline (also abbreviated as 2,2' or 2,2'-MDA) and 2,4'-methylenedianiline (also abbreviated as 2,4' or 2,4'-MDA) using 5 weight-% of a catalytic material and a solution comprising N,N'-diphenylmethylenediamine

| Catalyst | Reaction time (h) | Yield (%) | | | | | Isomer ratio |
| | | Total ABA | Total MDA | 2,2'-MDA | 2,4'-MDA | 4,4'-MDA | ≥3-ring | 4,4'/(2,2' + 2,4') |
|---|---|---|---|---|---|---|---|---|
| MCM-22 | 1 | 0.4 | 69.1 | 3.4 | 27.3 | 38.5 | 10.1 | 1.3 |
| | 5 | 0.0 | 84.9 | 4.2 | 35.1 | 45.6 | 15.0 | 1.2 |
| | 24 | 0.0 | 80.9 | 4.1 | 33.3 | 43.6 | 19.1 | 1.2 |
| Hf, Zn/SiO$_2$ | 1 | 25.4 | 17.3 | 0.0 | 3.3 | 14.0 | 6.2 | 4.2 |
| (Example 1) | 5 | 10.9 | 40.2 | 0.6 | 7.3 | 32.4 | 19.7 | 4.1 |
| | 24 | 2.2 | 56.5 | 1.5 | 11.7 | 43.4 | 17.5 | 3.3 |
| Hf, Zn/ | 1 | 2.2 | 69.1 | 0.6 | 12.3 | 56.2 | 12.3 | 4.4 |
| SiO$_2$·Al$_2$O$_3$ | 5 | 0.8 | 71.5 | 1.4 | 13.8 | 56.2 | 20.6 | 3.7 |
| (Example 2) | 24 | 0.0 | 73.0 | 1.9 | 15.2 | 55.9 | 25.1 | 3.3 |
| Zeolite Y | 1 | 5.3 | 60.6 | 0.7 | 8.6 | 51.3 | 6.2 | 5.5 |
| CBV-720 | 5 | 1.9 | 74.9 | 1.0 | 11.2 | 62.7 | 8.4 | 5.1 |
| (Zeolyst) | 24 | 0.5 | 77.0 | 1.4 | 13.5 | 62.2 | 14.2 | 4.2 |

First, N,N'-diphenylmethylenediamine (also abbreviated as aminal herein) was prepared by reacting aniline with an aqueous solution of formaldehyde (36 weight-% of formaldehyde in water) in a 3:1 molar ratio of aniline to formaldehyde, for 1 h at 50° C. After phase separation, the organic layer was isolated. 2.93 g of the organic layer was added to the dried catalyst in a sealed 10 mL glass vial. The mixture was then purged with nitrogen, placed in a heated metal block at 150° C., and stirred for 24 h with a Teflon-coated stirring bar. Samples (0.2 mL each) were taken after 1 h, 5 h, and 24 h. For work-up, the catalytic material was separated from the crude solution and the latter analyzed by gas chromatography. The results are shown in table 1.

Samples were analyzed by a Shimadzu 2010 gas chromatograph equipped with a CP-Sil 5 CB column (Agilent, 100% polydimethylsiloxane, 60 m, 0.25 μm film thickness, As can be seen from the results shown in table 1, the conventional MCM-22 reaches the highest yield of total MDA after 24 h. However, inventive catalytic materials Hf, Zn/SiO$_2$ (Example 1) and Hf, Zn/SiO$_2$·Al$_2$O$_3$ (Example 2) both providing also good yields of total MDA reach a higher isomer ratio 4,4'/(2,2'+2,4') than MCM-22. Zeolite Y achieved the best results in the testing with respect to the isomer ratio. However, the results shown in table 1 reflect the catalytic activity for a single cycle only.

Example 5: Recycling of a Catalytic Material 105.4 mg of a catalytic material according to Example 1 was dried overnight at 200° C. to afford 99.2 mg of a dried catalytic material. 1.97 g of the aminal solution as prepared in Example 4 was added to the dried catalytic material in a sealed 10 mL glass vial.

For a first reaction cycle, the mixture was then purged with nitrogen, placed in a heated metal block at a temperature of 150° C., and stirred for 24 h with a Teflon-coated stirring bar. The crude product solution was separated from the catalytic material and extracted for analysis by gas chromatography as described for Example 4.

For a second reaction cycle, 1.9 mL of the aminal-aniline solution as prepared in Example 4 was added to the catalytic material retained from the first reaction cycle (wet). The mixture was then purged with nitrogen, placed in a heated metal block at 150° C., and stirred for 24 h with a Teflon-coated stirring bar. Samples (0.2 mL each) were taken after 1 h, 5 h, and 24 h and analyzed as described in Example 4. For work-up, the catalytic material was separated from the crude solution and the latter analyzed by gas chromatography as described in Example 4.

Product extraction and analysis were repeated. In total, the catalytic material obtained from the initial cycle was subjected to 4 further consecutive 24 h reaction cycles with product extraction after each cycle. The results are shown in table 2. For comparative reasons, the same procedure has been carried out similarly using a conventional zeolite Y (CBV-720, Zeolyst), a catalytic material according to Examples 1, 2 and 3 as a catalytic material, whereby in total 7 consecutive cycles were run.

zeolite Y in the third recycling cycle. A similar behavior was observed for the yield of 4,4'-MDA. Further, it can be gathered from the results shown in table 2, that Hf Zn/SiO$_2$·Al$_2$O$_3$ according to Example 2 remained active for more reaction cycles compared to its all-silica counterpart according to Example 1. Though the isomer ratio was consistent over the cycles shown for Example 2, the lower isomer ratio indicates a lower selectivity towards the 4,4'-isomer. In addition to that, it can be seen from the results shown in table 2 that a catalytic material according to Example 3 wherein iron is supported on silica-alumina also shows a comparatively superior performance even after 7 consecutive cycles.

Comparative Example 6 and Examples 7 to 22:
Preparation of Catalytic Materials

Commercial zeolites were used in their proton form as oxidic support. Zeolite H-Y was obtained from Zeolyst International (CBV 720, Si/Al=15), H-MCM-22 from China Catalyst Group (Si/Al=14). The silica used as a oxidic support was acquired from Cabot (CAB-O-SIL® M-5), the alumina from Condea Chemie (PURALOX® NGa-150), and the silica-alumina from Grace (MS 13/110, 13% Al$_2$O$_3$).

TABLE 2

Results of the catalyzed preparation of 4,4'-methylenedianiline (also abbreviated as 4,4' or 4,4'-MDA), 2,2'-methylenedianiline (also abbreviated as 2,2' or 2,2'-MDA) and 2,4'-methylenedianiline (also abbreviated as 2,4' or 2,4'-MDA) using 5 weight-% of a (recycled) catalytic material and a solution comprising N,N'-diphenylmethylenediamine

| Catalyst | Cycle | Yield (%) | | | | | | Isomer ratio | Total yield of ABA, |
| | | Total ABA | Total MDA | 2,2'-MDA | 2,4'-MDA | 4,4'-MDA | ≥3-ring | 4,4'/(2,2' + 2,4') | MDA & ≥3-ring |
|---|---|---|---|---|---|---|---|---|---|
| Zeolite Y | 1 | 1.2 | 77.6 | 1.4 | 13.3 | 62.9 | 7.4 | 4.3 | 86.2 |
| CBV-720 | 2 | 10.2 | 34.5 | 0.5 | 5.4 | 28.7 | 4.0 | 4.9 | 48.7 |
| (Zeolyst) | 3 | 21.9 | 9.6 | 0.0 | 2.0 | 7.6 | 2.2 | 3.8 | 33.7 |
| | 4 | 24.5 | 7.6 | 0.3 | 1.6 | 5.7 | 1.3 | 3.0 | 33.4 |
| | 5 | 14.4 | 2.8 | 0.0 | 0.8 | 2.0 | 7.6 | 2.4 | 24.8 |
| Hf Zn/SiO$_2$ | 1 | 2.7 | 61.0 | 0.9 | 11.6 | 48.5 | 17.3 | 3.9 | 81.0 |
| (Example 1) | 2 | 4.7 | 59.1 | 0.7 | 11.0 | 47.4 | 16.5 | 4.0 | 80.3 |
| | 3 | 7.4 | 52.7 | 0.4 | 9.4 | 42.9 | 12.6 | 4.4 | 72.7 |
| | 4 | 18.4 | 43.6 | 0.5 | 7.8 | 35.4 | 7.2 | 4.3 | 69.2 |
| | 5 | 30.3 | 22.0 | 0.5 | 4.1 | 17.4 | 3.1 | 3.8 | 55.4 |
| Hf Zn/ | 1 | 0.0 | 77.8 | 1.9 | 16.2 | 59.6 | 22.2 | 3.3 | 100.0 |
| SiO$_2$•Al$_2$O$_3$ | 2 | 0.0 | 74.8 | 2.1 | 15.0 | 57.7 | 22.8 | 3.4 | 97.6 |
| (Example 2) | 3 | 0.0 | 76.7 | 2.3 | 15.4 | 59.0 | 23.3 | 3.3 | 100.0 |
| | 4 | 0.0 | 72.8 | 2.2 | 14.5 | 56.1 | 21.4 | 3.4 | 94.2 |
| | 5 | 0.1 | 75.0 | 2.2 | 14.7 | 58.1 | 21.0 | 3.4 | 96.1 |
| | 6 | 0.2 | 63.2 | 2.1 | 12.7 | 48.4 | 16.8 | 3.3 | 80.2 |
| | 7 | 0.4 | 64.1 | 2.0 | 12.2 | 49.8 | 17.5 | 3.5 | 82.0 |
| Fe/ | 1 | 0.0 | 72.4 | 1.8 | 15.1 | 55.4 | 18.7 | 3.3 | 91.1 |
| SiO$_2$•Al$_2$O$_3$ | 2 | 0.0 | 74.7 | 2.1 | 15.1 | 57.5 | 21.8 | 3.3 | 96.5 |
| (Example 3) | 3 | 0.1 | 73.5 | 2.2 | 14.8 | 56.5 | 22.0 | 3.3 | 95.7 |
| | 4 | 0.1 | 72.8 | 2.1 | 14.4 | 56.3 | 19.3 | 3.4 | 92.2 |
| | 5 | 0.2 | 72.6 | 2.0 | 14.2 | 56.4 | 19.0 | 3.5 | 91.8 |
| | 6 | 0.3 | 62.3 | 1.9 | 12.4 | 48.0 | 15.5 | 3.4 | 78.1 |
| | 7 | 1.1 | 61.1 | 1.8 | 11.3 | 47.9 | 14.2 | 3.6 | 76.4 |

As can be seen from the results in table 2, the yields dropped markedly after the first reaction cycle using zeolite Y whereas this was not the case for the catalytic material of the present invention. In contrast, the yield stayed almost constant for the first two cycles for the catalytic material according to Example 1, then decreased for the subsequent cycles. In its fifth recycling cycle the catalytic material achieved still more than twice as much of total MDA as For the metal-loaded catalysts, target amounts of the metal precursor salts were first dissolved in ultrapure water at room temperature; then respective amounts of the oxidic supports were added and the mixture was left stirring until the water evaporated. The resulting powder was dried at 60° C., then calcined in air at 500° C. for 2 h at a heating rate of 2° C./min to obtain the Comparative Example and Examples 7 to 22 as presented in Table 3.

TABLE 3

Overview of catalytic materials according to Comparative
Example 6 and Examples 7 to 18, including information
on the loading and the used precursor salts.

| # | Oxidic support | Supported material | Loading [weight-% based on total weight of oxidic support] | Precursor salt |
|---|---|---|---|---|
| Comp. Example 6 | SiO$_2$ | none | none | none |
| Example 7 | SiO$_2$ | La | 1.52 | La(NO$_3$)•6H$_2$O |
| Example 8 | SiO$_2$ | Ce | 1.73 | Ce(NO$_3$)$_3$•6H$_2$O |
| Example 9 | SiO$_2$ | Sc | 1.52 | Sc(NO$_3$)$_3$•xH$_2$O |
| Example 10 | SiO$_2$ | Ta | 1.32 | TaCl$_5$ (toluene used instead of water) |
| Example 11 | SiO$_2$ | Sn | 1.52 | Sn(CH$_3$CO$_2$)$_2$ |
| Example 12 | SiO$_2$ | Fe | 1.32 | Fe(NO$_3$)$_3$•9H$_2$O |
| Example 13 | SiO$_2$ | Zn | 1.73 | Zn(NO$_3$)$_2$•6H$_2$O |
| Example 14 | SiO$_2$ | Zr | 1.42 | ZrCl$_4$ |
| Example 15 | SiO$_2$ | Hf | 1.52 | HfCl$_4$ |
| Example 16 | SiO$_2$ | Hf | 2.78 | HfCl$_4$ |
| Example 17 | SiO$_2$ | Hf, Zn | 2.68, 0.52 | HfCl$_4$ and Zn(NO$_3$)$_2$•6H$_2$O |
| Example 18 | SiO$_2$ | Zr, Zn | 1.94, 0.31 | ZrCl and Zn(NO$_3$)$_2$•6H$_2$O |
| Example 19 | Al$_2$O$_3$ | Hf | 3.09 | HfCl$_4$ |
| Example 20 | SiO$_2$—Al$_2$O$_3$ | Hf | 3.09 | HfCl$_4$ |
| Example 21 | Zeolite MCM-22 | Hf | 3.09 | HfCl$_4$ |
| Example 22 | Zeolite Y | Hf | 3.09 | HfCl$_4$ | stirred and heated at 50° C. Formaldehyde (274 mL, VWR Chemicals, 36% in aqueous solution, stabilized with methanol) was added dropwise until the mixture reached an aniline/formaldehyde (A/F) molar ratio of 3. The mixture was stirred for a further 1 h at 50° C. The aminal solution was collected in the organic layer and the aqueous layer was discarded by phase separation of the mixture. The NF ratio was determined by proton nuclear magnetic resonance spectroscopy ($^1$H NMR). The NMR spectra were recorded on a Bruker AVANCE III HD 400 MHz Spectrometer and CDCl$_3$ (Sigma-Aldrich, 99.8 atom % D) was used as the solvent.

The aminal solution was added to the dried catalytic material in a sealed vial, later purged with nitrogen. Typically, 200 mg of dried catalytic material was used in the experiments, representing 5 weight-% with respect to the aminal. The mixture was stirred and maintained at 150° C. unless stated otherwise for the required reaction time. Aliquots of ≤100 microL were taken at different time points, and the spent catalyst was separated from the crude product solution by centrifugation. The crude product was then analyzed by gas chromatography (GC). Tetrahydrofuran (Acros Organics, 99+% extra pure) was used to dilute the crude solution and nitrobenzene (Fluka, >99.5% purity) was added as an external standard. Reaction samples were analysed in a Shimadzu 2010 gas chromatograph equipped with a 60 m CP-Sil 5 CB column and an FID detector. Compounds were identified with known compounds and gas chromatography-mass spectrometry (GC-MS).

The results of the catalytic testing are presented in Table 4.

TABLE 4

Overview of yields and isomer ratios of the MDA synthesis products at 150° C. over
catalytic materials, wherein 5 weight-% catalytic material were used and a reaction
time of 24 h was applied. The yields of o-ABA and p-ABA were combined into a
single ABA value (ABA), whereas the MDA yield represents the summed
yields of the three MDA isomers.

| # | Catalytic material | ABA [%] | MDA [%] | OMDA [%] | 4,4'/(2,2' + 2,4') |
|---|---|---|---|---|---|
| Comp. Example 6 | SiO$_2$ | 22.8 | 10.0 | — | 3.6 |
| Example 7 | 1.52 wt.-% La on SiO$_2$ | 13.7 | 30.1 | 3.6 | 4.6 |
| Example 8 | 1.73 wt.-% Ce on SiO$_2$ | 16.5 | 25.0 | — | 3.8 |
| Example 9 | 1.52 wt.-% Sc on SiO$_2$ | 3.8 | 48.8 | 10.8 | 4.0 |
| Example 10 | 1.32 wt.-% Ta on SiO$_2$ | 17.7 | 21.3 | — | 4.2 |
| Example 11 | 1.52 wt.-% Sn on SiO$_2$ | 4.7 | 37.3 | 5.1 | 4.1 |
| Example 12 | 1.32 wt.-% Fe on SiO$_2$ | 6.1 | 55.4 | 10.8 | 4.3 |
| Example 13 | 1.73 wt.-% Zn on SiO$_2$ | 27.0 | 26.7 | — | 4.8 |
| Example 14 | 1.42 wt.-% Zr on SiO$_2$ | 2.1 | 53.8 | 12.9 | 3.4 |
| Example 15 | 1.52 wt.-% Hf on SiO$_2$ | 5.9 | 46.5 | 15.1 | 4.0 |
| Example 16 | 2.78 wt.-% Hf on SiO$_2$ | 3.1 | 52.7 | 14.6 | 3.4 |
| Example 17 | 2.68 wt.-% Hf and 0.52 wt.-% Zn on SiO$_2$ | 3.8 | 51.5 | 16.5 | 4.0 |
| Example 18 | 1.94 wt.-% Zr and 0.31 wt.-% Zn on SiO$_2$ | 3.6 | 52.3 | 15.4 | 3.0 |

Example 23: Preparation of 4,4'-methylenedianiline, 2,2'-methylenedianiline, and 2,4'-methylenedianiline by Conversion of Aniline and Formaldehyde Catalytic materials according to Comparative Example 6 and Examples 7 to 22 were dried overnight at 200° C. before use in synthesis of MDA.

An aminal solution was prepared by non-catalyzed condensation reaction between aniline and formaldehyde, and was used as starting material in the acid-catalyzed synthesis of MDA, as follows. In a 2 L two-necked round bottom flask, aniline (980 mL, Acros Organics, 99.8% purity) was As can be gathered from the results in Table 4, unloaded SiO$_2$ only produced MDA in a 10%. Three rare-earth elements were studied, La, Ce and Sc. La$_{1.52}$/SiO$_2$ (Ex. 7) and Ce$_{1.73}$/SiO$_2$ (Ex. 8) showed a moderate activity (30% and 25% MDA yield, respectively). This activity was improved with Sc$_{1.52}$/SiO$_2$ (Ex. 9). A transition metal like Ta (Ex. 10) and a post-transition metal like Sn (Ex. 11), which are often used in other Lewis acid-catalysed transformations, were able to form MDA in modest yields (37% MDA yield with Sn$_{1.52}$/SiO$_2$, see Ex. 11). Zn$_{1.73}$/SiO$_2$ (Ex. 13) showed a comparatively better performance as catalyst (27% yield of MDA and 4,4'-MDA/(2,2'-MDA+2,4'-MDA) isomer ratio of 4.8) and further enhanced with $Fe_{1.32}/SiO_2$ (Ex. 12) achieving 55% yield of MDA and an isomer ratio 4,4'-MDA/(2,2'-MDA+2,4'-MDA) of 4.3. The best results were attained when other Lewis acids were employed. Both $Zr_{1.42}/SiO_2$ (Ex. 14) and $Hf_{1.52;2.78}/SiO_2$ (Ex. 15-16) were found to be outstanding catalytic materials for the synthesis of MDA, achieving high MDA and OMDA yields and a respectable 4,4'-MDA/(2,2'-MDA+2,4'-MDA) isomer ratio. Remarkably, the introduction of even a small loading of Zn (0.52 weight-% in Ex. 17, 0.31 weight-% in Ex. 18) increased both the OMDA yield and the isomer ratio with only a minor drop in MDA yield.

As can be seen from the further results in FIG. 2, an improvement was seen when supports with some Brønsted acid character such as alumina ($Al_2O_3$) and silica-alumina ($SiO_2$—$Al_2O_3$) were employed, particularly in the case of silica-alumina, with a marked increase in the catalytic activity and higher MDA and OMDA yields obtained after just 1 h of reaction. Complete conversion was achieved as indicated by the absence of the ABA intermediates. The parent zeolites, H-MCM-22 and H-Y, were also tested as supports. For $Hf_{3.09}/MCM-22$ (Ex. 21), this resulted in slightly higher ABA and OMDA contents, similar MDA yields, as well as a slightly higher 4,4'-MDA/(2,2'-MDA+2,4'-MDA) isomer ratio, compared to that obtained with the parent H-MCM-22 zeolite. As for $Hf_{3.09}/Y$ (Ex. 22), all the values were very similar to those obtained with its metal-free counterpart, which seems to suggest that the addition of a metal, at least in the case of Hf, did not change the catalytic behaviour of zeolite H-Y.

CITED LITERATURE

Figure 1:
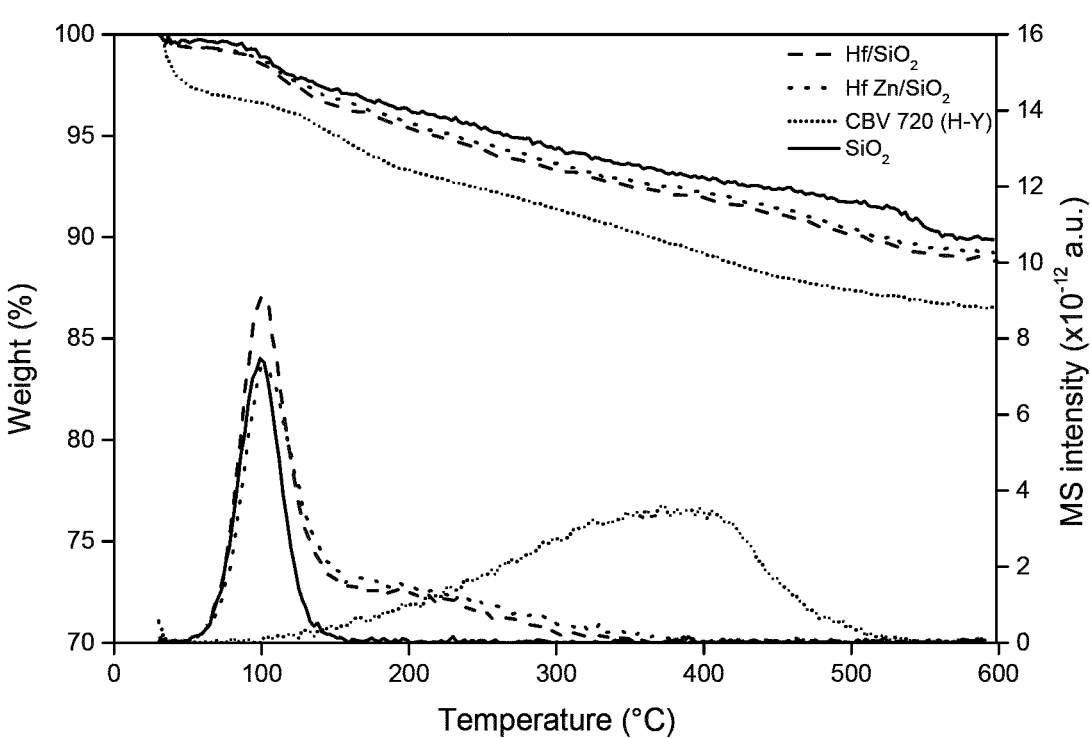
FIG. 1: shows the profiles from thermogravimetric analysis (scatter plots, upper graphs) and the aniline-sample interaction strength (line plots, lower graphs) of $Hf/SiO_2$, Hf $Zn/SiO_2$, CBV 720 (zeolite H-Y), and $SiO_2$ investigated by monitoring the m/z value of 93 (corresponding to aniline, $C_6H_5NH_2$).
Figure 2:
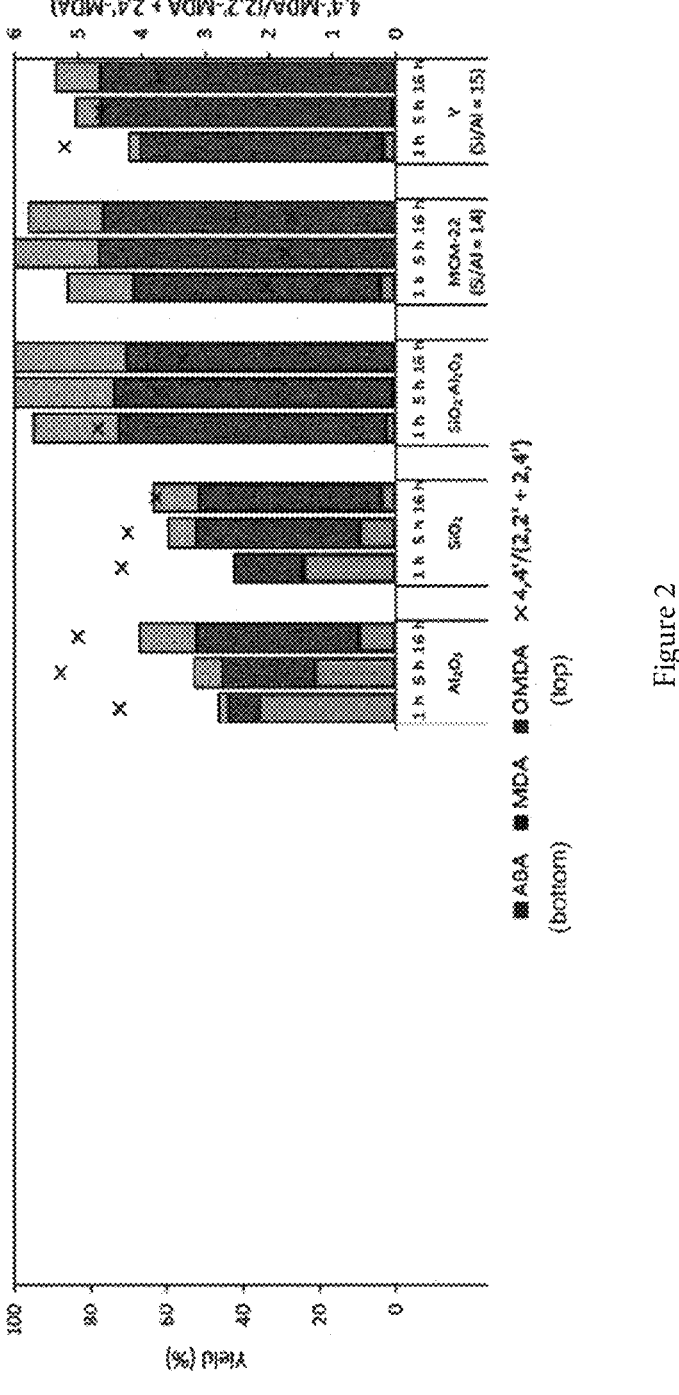
FIG. 2: shows the product yields obtained in MDA synthesis using Hf loaded on various oxidic supports as catalytic materials, where the synthesis was performed at 150° C., using 5 weight-% catalyst. The 4,4'-MDA/(2,2'-MDA+2,4'-MDA) isomer ratio is indicated by the crosses (x), the ABA yield is shown in the lower part of the respective bar, the MDA yield is shown in the middle part of the respective bar, and the OMDA yield is shown in the upper part of the respective bar, wherein the yield is given in %.

WO 2016/005269 A1
EP 3 263 547 A1
JP 2012-131720 A
JP 2013-095724 A
JP 2012-250971 A
WO 2010/019844 A1
WO 2010/072504 A1
M. Haus et al. "Advanced kinetic models through mechanistic understanding: Population balances for methylenedianiline synthesis" in Chemical Engineering Science 2017, vol. 167, p. 317
D. Jin et al. "Dramatic change of methylenedianiline activity and selectivity in different pore geometry of zeolites" in Microporous and Mesoporous Materials 2016, vol. 233, p. 109-116
C. A. Emeis "Determination of integrated molar extinction coefficients for infrared absorption bands of pyridine adsorbed on solid acid catalysts" in Journal of Catalysis 1993, vol. 141, p. 347-354
M. Velthoen et al. "Probing acid sites in solid catalysts with pyridine UV-Vis spectroscopy" in Physical Chemistry Chemical Physics 2018, vol. 20, p. 21647-21659

The invention claimed is:

1. A catalytic material for use in the preparation of one or more of 4,4'-methylenedianiline, 2,2'-methylenedianiline, 2,4'-methylenedianiline, and oligomers of two or more thereof, the catalytic material comprising an oxidic support, wherein the oxidic support comprises titania, zirconia, alumina, or silica, and further comprising a supported material supported on the oxidic support, wherein the supported material comprises an element $E_{SM1}$ selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb, and mixtures of two or more thereof, the catalytic material exhibiting a Brønsted acid site density of equal or less than 100 μmol/g, wherein the Brønsted acid site density is determined by pyridine adsorption using FTIR spectroscopy.

2. The catalytic material of claim 1, wherein $E_{SM1}$ is selected from the group consisting of Sc, Y, La, Ce, Nd, Pr, Hf, Cr, Fe, Co, Ni, Cu, Zn, Pb, Zr, and mixtures of two or more thereof.

3. The catalytic material of claim 1, wherein the catalytic material comprises $E_{SM1}$, calculated as element, in an amount in the range of from 0.1 to 10 weight-%, based on the total weight of the oxidic support.

4. The catalytic material of claim 1, wherein the supported material further comprises an element $E_{SM2}$ selected from groups 3-14 of the periodic system of elements, rare earth metals, and mixtures of two or more thereof, wherein $E_{SM2}$ is different to $E_{SM1}$.

5. The catalytic material of claim 4, wherein $E_{SM2}$ is selected from groups 3, 4, 5, 6, 8, 10, 11, 12, 14, rare earth metals, and mixtures of two or more thereof.

6. The catalytic material of claim 4, wherein the catalytic material comprises $E_{SM2}$, calculated as element, in an amount in the range of from 0.1 to 3 weight-%, based on the total weight of the oxidic support.

7. The catalytic material of claim 1, wherein from 95 to 100 weight-% of the catalytic material consists of the oxidic support and the supported material, based on the total weight of the catalytic material.

8. The catalytic material of claim 1, having a mesopore volume $V_{meso}$ in the range of from 0.50 to 1.30 cm³/g, wherein the mesopore volume is determined according to the Barrett-Joyner-Halenda (BJH) method.

9. The catalytic material of claim 1, exhibiting an acid site density in the range of from 0.050 to 1.000 mmol/g, as determined by temperature-programmed-desorption of $NH_3$ ($NH_3$-TPD).

10. A process for the preparation of the catalytic material of claim 1, the process comprising:
   (i) preparing a mixture comprising a liquid solvent system, a source of an oxidic support comprising titania, zirconia, alumina, or silica, a source of an element $E_{SM1}$ selected from the group consisting of Ti, Zr, V, Nb, Ta, Mo, W, Ge, Sn, Sc, Y, La, Ce, Nd, Pr, Hf, Cr, Fe, Co, Ni, Cu, Zn, Pb, and mixtures of two or more thereof, and optionally a source of an element $E_{SM2}$ selected from groups 3-14 of the periodic system of elements, rare earth metals, and mixtures of two or more thereof, wherein the optional $E_{SM2}$ is different to $E_{SM1}$, obtaining a precursor of the catalytic material; and (ii) calcining the precursor of the catalytic material in a gas atmosphere, obtaining the catalytic material.

11. A catalytic material obtainable and/or obtained by the process of claim 10.

12. A process for the preparation of one or more of 4,4'-methylenedianiline, 2,2'-methylenedianiline, 2,4'-methylenedianiline, and oligomers of two or more thereof, the process comprising:

(1) providing a reactor comprising a reaction zone, wherein the reaction zone comprises a catalytic material according to claim 1;

(2) providing a feed into the reaction zone according to (1), wherein the feed comprises one or more of aniline, formaldehyde, and N,N'-diphenylmethylenediamine;

(3) converting the feed under reaction conditions in the reaction zone; obtaining a product mixture comprising one or more of 4,4'-methylenedianiline, 2,2'-methylenedianiline, 2,4'-methylenedianiline, and oligomers of two or more thereof; and (4) separating the product mixture from the reaction zone.

13. The catalytic material of claim 1, having a BET specific surface area $S_{BET}$ in a range from 100 to 310 m$^2$/g, wherein the BET specific surface area $S_{BET}$ is determined according to BET method.

\* \* \* \* \*